United States Patent
Blidner

(10) Patent No.: US 12,365,943 B2
(45) Date of Patent: Jul. 22, 2025

(54) SYSTEMS AND METHODS FOR NEXT GENERATION SEQUENCING UNIFORM PROBE DESIGN

(71) Applicant: Tempus AI, Inc., Chicago, IL (US)

(72) Inventor: Richard Blidner, Chicago, IL (US)

(73) Assignee: Tempus AI, Inc., Chicago, IL (US)

( * ) Notice: Subject to any disclaimer, the term of this patent is extended or adjusted under 35 U.S.C. 154(b) by 1101 days.

(21) Appl. No.: 17/323,986

(22) Filed: May 18, 2021

(65) Prior Publication Data

US 2021/0269878 A1    Sep. 2, 2021

Related U.S. Application Data

(62) Division of application No. 17/076,704, filed on Oct. 21, 2020, now Pat. No. 11,041,200.

(60) Provisional application No. 62/924,073, filed on Oct. 21, 2019.

(51) Int. Cl.
*C12Q 1/6874*    (2018.01)
*C12Q 1/6883*    (2018.01)
*C40B 40/06*    (2006.01)

(52) U.S. Cl.
CPC ......... *C12Q 1/6874* (2013.01); *C12Q 1/6883* (2013.01); *C40B 40/06* (2013.01)

(58) Field of Classification Search
None
See application file for complete search history.

(56) References Cited

U.S. PATENT DOCUMENTS 10,781,480 B1    9/2020  Noor et al.
2018/0201994 A1  7/2018  Beauchamp et al.

FOREIGN PATENT DOCUMENTS

WO    WO 2005/010200 A2    2/2005
WO    WO-2018136526 A1 *   7/2018  .......... B01J 19/0046

OTHER PUBLICATIONS

Gaudin, et al. "Hybrid Capture-Based Next Generation Sequencing and Its Application to Human Infectious Diseases", Frontiers in Microbiology, Nov. 2018, vol. 9, Article 2924, pp. 1-9.

* cited by examiner

*Primary Examiner* — Kaijiang Zhang
(74) *Attorney, Agent, or Firm* — MORGAN, LEWIS & BOCKIUS LLP

(57) ABSTRACT

Systems and methods are provided for determining an optimized probe set. The method proceeds by obtaining a set of probes, where each probe has a respective concentration. The set of probes is assayed against a sample library, and at least i) a respective recovery rate for each probe in the set of probes, and ii) a median recovery rate for the set of probes are obtained. Modify the respective concentration of each probe that does not satisfy predetermined recovery rate threshold. Reevaluate the set of probes against the sample library. Repeat the modifying and reevaluation until the respective updated recovery rate for each probe in the updated set of probes satisfies the predetermined recovery rate threshold, thereby providing the optimized set of probes for the sample library.

31 Claims, 9 Drawing Sheets

SYSTEMS AND METHODS FOR NEXT GENERATION SEQUENCING UNIFORM PROBE DESIGN

CROSS-REFERENCE TO RELATED APPLICATIONS

This application is a divisional patent application of U.S. patent application Ser. No. 17/076,704, filed Oct. 21, 2020, which claims the benefit of U.S. Provisional Application No. 62/924,073, filed on Oct. 21, 2019, which is expressly incorporated by reference in its entirety for all purposes.

TECHNICAL FIELD

The present disclosure relates generally to designing efficient probes for use in next generation sequencing.

BACKGROUND

One aspect of the design of next generation sequencing assays is the selection and concentration of probes used to identify specific regions of a genome.

In the prior art, one method of reducing probe concentration is to add the reverse complement of each over-performing probe, thereby effectively subtracting a certain percentage of such over-performing probes from an existing probe pool. Another method of setting probe concentration is to utilize an array-based platform. Some methods known in the prior art make use of probe sub-pools, which are formulated at known equimolar concentrations. This enables the modular use of sub-pools (e.g., each sub-pool is distinct and can be modified separately from the other sub-pools).

What is needed in the field are improved methods of altering probe concentrations to produce probe pools that are optimized for particular samples.

SUMMARY

Given the background above, improved systems and methods are needed for improved probe design, in particular for use with targeted next-generation sequencing. Advantageously, the present disclosure provides solutions to these and other shortcomings in the art. For instance, in some embodiments, the systems and methods described herein leverage multiple methods of probe modification to improve the overall coverage rate of a set of probes.

As disclosed herein, any embodiment disclosed herein when applicable can be applied to any other aspect.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Figure 1:
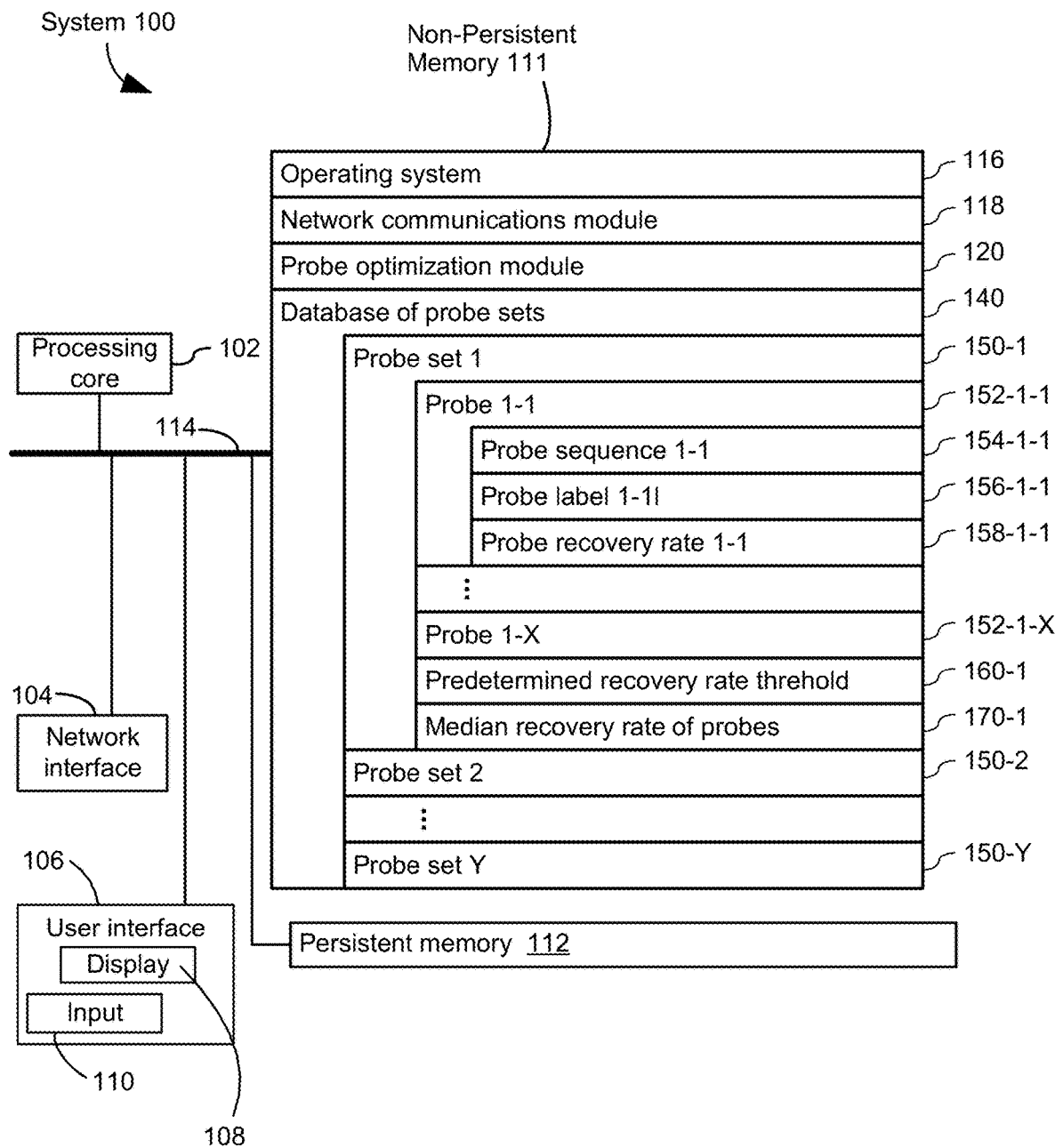
FIG. 1 illustrates a block diagram of an example computing device, in accordance with some embodiments of the present disclosure.

Sequencing depth is one method to measure probe performance. Alternative methods include measuring the number of reads associated with a target region or portion of a target region.

Like reference numerals refer to corresponding parts throughout the several views of the drawings.

DETAILED DESCRIPTION

The methods described herein provide for optimizing a probe set for improved performance (e.g., with regards to a specific patient). In particular, the methods described herein provide for decreasing the effective concentration of one or more over-performing probes. In some embodiments, this is achieved by suppressing the capture rate of one or more over-performing probes by adjusting the ratio of labeled and unlabeled probe present in the set of probes used to assay a patient sample (e.g., for an individual probe, 30% of the probe molecules could be labeled with biotin while the remaining 70% of molecules are unlabeled). This suppression by capture method is novel to the art, and can be combined with other methods to increase or decrease the effective concentration of over- or under-performing probes (for example, adding locked nucleic acid/LNA or similar modifications to a portion of the probes, using hairpins, using interfering oligos, using HABA/4'-hydroxyazobenzene-2-carboxylic acid to interfere with streptavidin, using other probe immobilizers, interfering with hybridization kinetics, using other methods of adjusting the effective or functional concentration/molarity of the probe, etc.) in order to produce highly optimized probe sets with even capture rates (e.g., coverage). The systems and methods may also be combined with methods to reduce the amplification of certain RNA or DNA molecules during sequencing library generation (For example, blocking RNAs, knocking down RNA transcripts, and/or using siRNA, CRISPR, RNAse, etc. to reduce reads of certain nucleic acid molecules, for example, mRNA transcripts associated with highly expressed genes).

Definitions.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "comprising," or any variation thereof, when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the terms "subject" or "patient" refers to any living or non-living human (e.g., a male human, female human, fetus, pregnant female, child, or the like). In some embodiments, a subject is a male or female of any stage (e.g., a man, a woman or a child).

As used herein, the terms "single nucleotide variant," "SNV," "single nucleotide polymorphism," or "SNP" refer to a substitution of one nucleotide to a different nucleotide at a position (e.g., site) of a nucleotide sequence, for example, a sequence read from an individual. A substitution from a first nucleobase X to a second nucleobase Y may be denoted as "X>Y." For example, a cytosine to thymine SNP may be denoted as "C>T." The term "het-SNP" refers to a heterozygous SNP, where the genome is at least diploid and at least one—but not all—of the two or more homologous sequences exhibits the particular SNP. Similarly, a "hom-SNP" is a homologous SNP, where each homologous sequence of a polyploid genome has the same variant compared to the reference genome. As used herein, the term "structural variant" or "SV" refers to large (e.g., larger than 1 kb) regions of a genome that have undergone physical transformations such as inversions, insertions, deletions, or duplications (e.g., see review of human genome SVs by Spielmann et al., 2018, Nat Rev Genetics 19:453-467).

As used herein, the term 'indel' refers to insertion and/or deletion events of stretches of one or more nucleotides, either within a single gene locus or across multiple genes.

As used herein, the term "copy number variant," "CNV," or "copy number variation" refers to regions of a genome that are repeated. These may be categorized as short or long repeats, in regards to the number of nucleotides that are repeated over the genome regions. Long repeats typically refer to cases where entire genes, or large portions of a gene, are repeated one or more times.

As used herein, the term "mutation," refers to a detectable change in the genetic material of one or more cells. In a particular example, one or more mutations can be found in, and can identify, cancer cells (e.g., driver and passenger mutations). A mutation can be transmitted from a parent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that are added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as an mRNA transcript or a genomic locus.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, for example, using sequencing techniques or using probes, for example, in hybridization arrays or capture probes, or amplification techniques, such as the polymerase chain reaction (PCR) or linear amplification using a single primer or isothermal amplification.

As used herein, the term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term "read-depth," "sequencing depth," or "depth" refers to a total number of read segments from a sample obtained from an individual at a given position, region, or locus. The locus can be as small as a nucleotide, or as large as a chromosome arm, or as large as an entire genome. Sequencing depth can be expressed as "Yx", for example, 50x, 100x, etc., where "Y" refers to the number of times a locus is covered with a sequence read. In some embodiments, the depth refers to the average sequencing depth across the genome, across the exome, or across a targeted sequencing panel. Sequencing depth can also be applied to multiple loci, the whole genome, in which case Y can refer to the mean number of times a loci or a haploid genome, a whole genome, or a whole exome, respectively, is sequenced. When a mean depth is quoted, the actual depth for different loci included in the dataset can span over a range of values. Ultra-deep sequencing can refer to at least 100x in sequencing depth at a locus.

As used herein, the term "reference exome" refers to any particular known, sequenced, or characterized exome, whether partial or complete, of any tissue from any organism or pathogen that may be used to reference identified sequences from a subject. Exemplary reference exomes used for human subjects, as well as many other organisms, are provided in the online GENCODE database hosted by the GENCODE consortium, for instance Release 29 (GRCh38.p12) of the human exome assembly.

As used herein, the term "reference genome" refers to any particular known, sequenced or characterized genome, whether partial or complete, of any organism or pathogen that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes or genetic sequences. In some embodiments, a reference genome includes sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "sample" refers to a biological sample obtained from a subject (e.g., a patient). In some embodiments, a sample comprises blood, cfDNA, saliva, solid tissue, or FFPE tissue.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Example System Embodiments.

Now that an overview of some aspects of the present disclosure and some definitions used in the present disclosure have been provided, details of an exemplary system are described in conjunction with FIG. 1. FIG. 1 is a block diagram illustrating a system 100 in accordance with some implementations. The system 100 in some implementations includes one or more processing units CPU(s) 102 (also referred to as processors), one or more network interfaces 104, a user interface 106 including (optionally) a display 108 and an input system 110, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the system 100 with other devices and/or a communication network 104;
- a probe optimization module 120 for determining an optimized set of probes for use against a sample (e.g., a nucleic acid sample from a patient); and
- a database 140 of probe sets comprising, for each probe set 150, information for each probe 152 in a set of one or more probes including the respective sequence 154, optionally a respective label 156, and a respective recovery rate 158 resulting from assaying the respective probe against a sample library; each probe set 150 further includes a predetermined recovery rate threshold 160 (e.g., for determining which probes in the respective probe set could be optimized) and a median recovery rate of probe 170 across the respective probe set.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Although FIG. 1 depicts a "system 100," the figure is intended more as a functional description of the various features that may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules instead may be stored in persistent memory 112.

Optimization of Probe Sets

Figure 2:
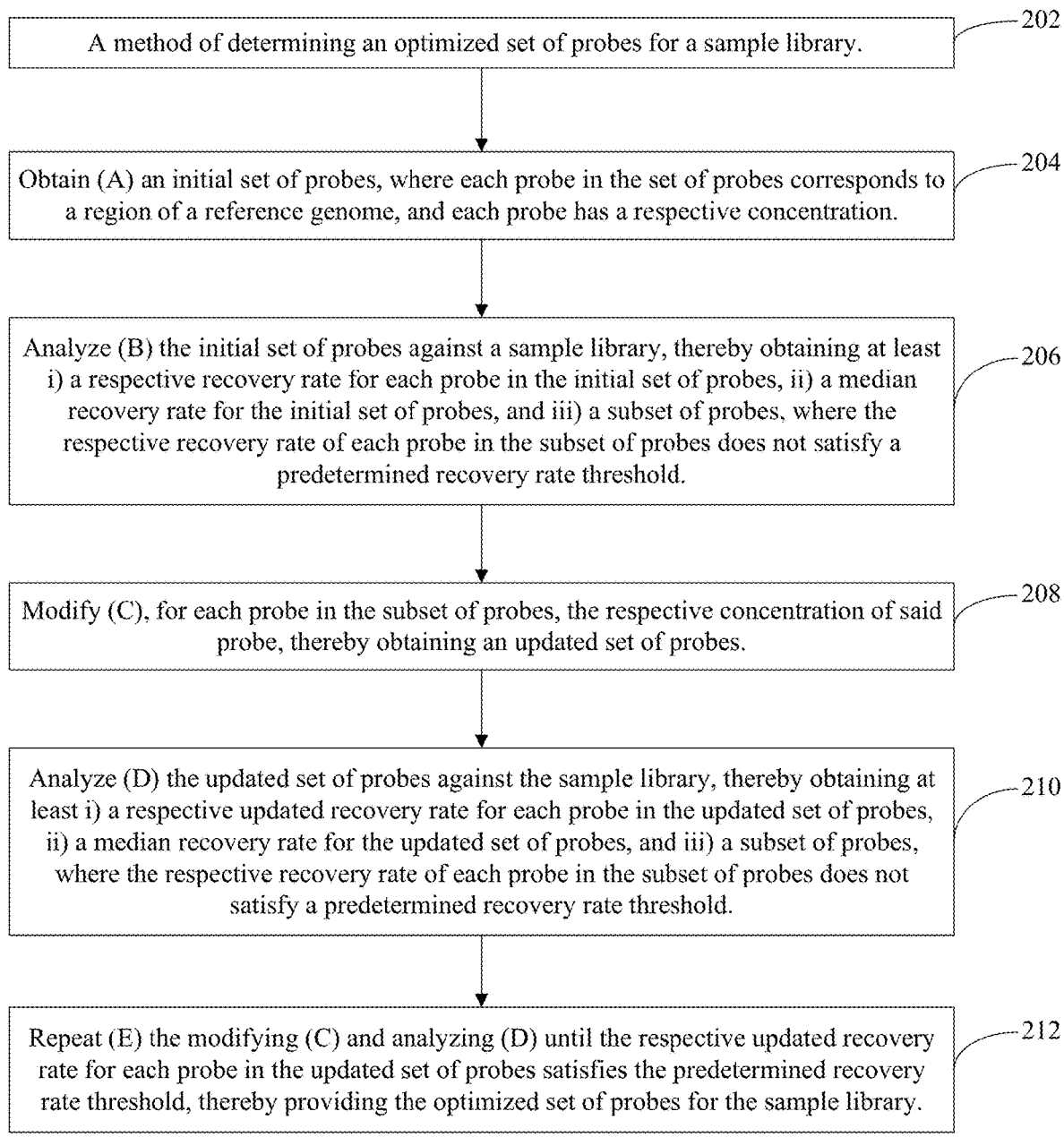
FIG. 2 provides a flow chart of processes and features for determining an optimized set of probes for sequencing, in accordance with some embodiments of the present disclosure.

While a system in accordance with the present disclosure has been disclosed with reference to FIG. 1, methods in accordance with the present disclosure are now detailed below with reference to FIGS. 2 and 3A-3D. FIG. 2 provides an example outline of the methods described herein. FIGS. 3A-3D each provide illustrations of methods of probe set construction.

In some embodiments, the method comprises designing a genome assay by modifying the number and/or concentration of probes. In some embodiments, the steps of the method include 1) assaying the set of probes against a sample (e.g., a single patient sample, a reference sample, a collection of samples, etc.), 2) identifying probes with higher or lower recovery rates than the median recovery rate of the set of probes, 3) reducing the concentration of probes with a higher recovery rate than the median recovery rate and/or increasing the concentration of probes with a lower recovery rate than the median recovery rate, and 4) assaying the updated set of probes against the same or a substantially similar sample.

In some embodiments, the method proceeds as outlined in FIG. 2 and as described below.

Block 202. Referring to block 202, in some embodiments, the method determines an optimized set of probes for enriching a sample library (e.g., or sample libraries) preparatory to sequencing. In some embodiments, the sample library is for a single patient. In some embodiments, the sample library is for a plurality of patients. In some embodiments, the sample library is an exome panel (e.g., a backbone).

Block 204. Referring to block 204, in some embodiments, the method proceeds, by obtaining an initial set of probes, where each probe in the initial set of probes corresponds to a region of a reference genome or reference exome, and each probe has a respective concentration (e.g., molar concentration). In some embodiments, the initial set of probes is for sequencing the sample library with a predetermined mean read depth.

In some embodiments, each probe in the initial set of probes is present at a same concentration (e.g., the probes are present in equimolar concentration). In some embodiments, one or more probes in the set of probes are present in a different concentration (e.g., the molar concentration of one or more probes is varied).

In some embodiments, a whole exome backbone is used as the reference exome, and the set of probes comprises a plurality of probes that are present at a first probe concentration (e.g., to obtain a predetermined read depth), and at least one spike-in probe (e.g., for one or more specific targets) that are each present at a higher concentration than the first probe concentration (e.g., to obtain a higher read depth). In some embodiments, the first probe concentration is 0 (e.g., there are no probes other than the at least one spike-in probes present in the set of probes).

In some embodiments, the set of probes comprises i) a first subset of probes used to sequence the exome (e.g., the "backbone"), where each probe in the first subset of probes has a read depth of 75×, and ii) at least one spike-in probe with a read depth higher than 75×. In some embodiments, the higher read depth comprises at least 100×, at least 125×, at least 150×, at least 200×, at least 250×, at least 300×, at least 400×, at least 450×, at least 500×, or at least 550×.

In some embodiments, the at least one spike-in probes are targeted for sequencing loci associated with inherited cancer risks. In some embodiments, the at least one spike-in probes are to identify copy number variants, indels, and/or other mutations at particular loci. In some embodiments, each spike-in probe has a different read depth. In some embodiments, each probe in a probe set is associated with a specific cancer sub-type (e.g., each probe serves to help identify subjects that may have or be predisposed to have a particular cancer sub-type). In some embodiments, the optimized probe set targets specific areas of a reference genome (e.g., intron regions, exon region, immunology regions, or regions associated with susceptibility to or infection from a virus, bacteria, or other pathogen).

Block 206. Referring to block 206, in some embodiments, the method continues by analyzing the set of probes against a sample library, thereby obtaining at least i) a respective recovery rate (e.g., coverage) for each probe in the set of probes, ii) a median recovery rate (e.g., median coverage) for the set of probes, and iii) a subset of probes, where the respective recovery rate of each probe in the subset of probes does not satisfy a predetermined recovery rate threshold.

Figure 3A:
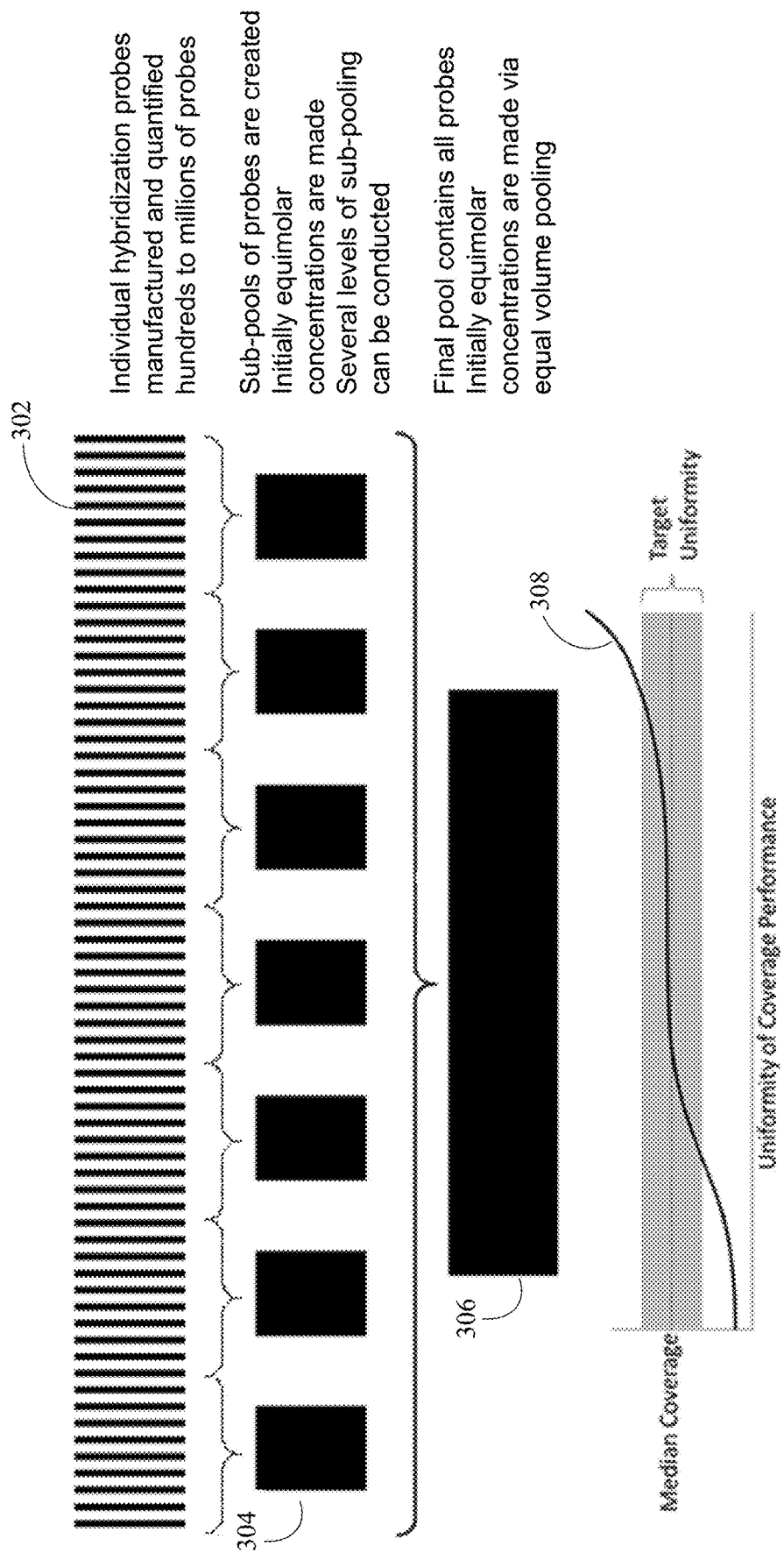
FIGS. 3A, 3B, 3C, and 3D collectively illustrate examples of how sets of probes may be modified through the use of sub-pools, in accordance with some embodiments of the present disclosure.

For example, as shown in FIG. 3A a plurality of probes 302 are combined into one or more sub-pools 304 of probes. These sub-pools 304 are then combined into a final set 306 of probes. The use of sub-pools enables finer tuning of the concentration of the different probes. In some embodiments, equal amounts of each sub-pool are combined to produce the final probe set. In some embodiments, one or more sub-pools are added at differing amounts to produce the final probe set. In some embodiments, equal amounts of each probe are present in each sub-pool and then also in the final probe set. In some embodiments, equal amounts of each probe are present in each sub-pool, but differing amounts of each sub-pool are combined to produce the final probe set. In some embodiments, one or more probes are present in the sub-pools at differing amounts.

Block 208. Referring to block 208, in some embodiments, the method continues by modifying, for each probe in the subset of probes, the respective concentration of said probe, thereby updating the set of probes. In some embodiments, modifying the concentration of one or more probes in the initial probe set comprises reducing the effective concentration of the one or more probes in the updated set of probes.

After assaying the final probe set against a sample library (e.g., a patient sample), the coverage (e.g., recovery rate) 308 for each probe is determined, and a median coverage rate can be calculated. In some embodiments, there is a target level of coverage for each probe (e.g., a tolerance of either over- or under-coverage). Over- and/or under-performing probes can then be identified from this first assay based on whether the respective recovery rate for each probe is above or below a predetermined threshold from the median coverage rate.

In some embodiments, each probe in the set of probes includes an attached label (e.g., each probe in the initial set of probes is biotinylated). See e.g., Miyazato et al. 2016 Scientific Reports 6, 28324. In some embodiments, each probe in the initial set of probes is unlabeled.

In some embodiments the attached label can be selectively captured from solution. The attached moiety can be a mixture of selective moieties that affect the capture or selection of the probe. Where by attached labels can be modulated bind and hold or interfere with binding or lack of binding, modulation of the kinetics of binding different probes with attach labels with different affinities. Binding moieties are not limited in scope of association; these could be covalent bonds, ionic bonding, polar covalent bonds, vander waal forces, hydrogen bonding, or electrostatic forces. These attached labels could include chemical alterations that affect the binding strength, alterations to the binding conditions, or alterations to the kinetics of the binding. Binding moieties could be modulated in concentration or type to affect selection of the desired probe. A plurality of binding moieties could be employed to modulate the effective capture of different groups of probes. The binding moieties could also be absent on the probe to modulate the effective population captured. Attached labels could also include a chemical cleavage group to modulate the effective capture of the probes. Examples of binding moieties include but are not limited to biotin:streptavidin, biotin:avidin, biotin:haba:streptavidin, antibody:antigen, antibody:antibody, covalent chemical linkage (ex. click chemistry).

In some embodiments binding moieties can be attached to a solid support, chemically modified linkers or in solution. Attachment labels can be attached to probes terminal groups or on the internal structure of the probe.

Block 210. Referring to block 210, in some embodiments, the method proceeds by analyzing the updated set of probes against the sample library, thereby obtaining at least i) a respective updated recovery rate for each probe in the updated set of probes, ii) a median recovery rate for the updated set of probes, and iii) a subset of probes, where the respective recovery rate of each probe in the subset of probes does not satisfy a predetermined recovery rate threshold.

In some embodiments, decreasing the concentration of over-performing probes comprises simply altering the total concentration of over-performing probes in the final set of probes. In some embodiments, the concentration of over-performing probes can be effectively decreased by decreasing the concentration of labeled over-performing probe. In embodiments where the initial set of probes includes unlabeled probes, the concentration of each over-performing probe can be corrected (e.g., adjusted so that all probes satisfy a predefined recovery rate threshold) by adding labeled (e.g., biotinylated) versions of each over-performing probe in proportion with labeled amounts of other probes in the probe set (e.g., to achieve even capture rates for each probe in the probe set). In some embodiments, the concentration of one or more over-performing probes can be reduced by reducing the percentage of over-performing probes that are biotinylated (e.g., by remaking each respective sub-pool that includes an over-performing probe).

Figure 3B:
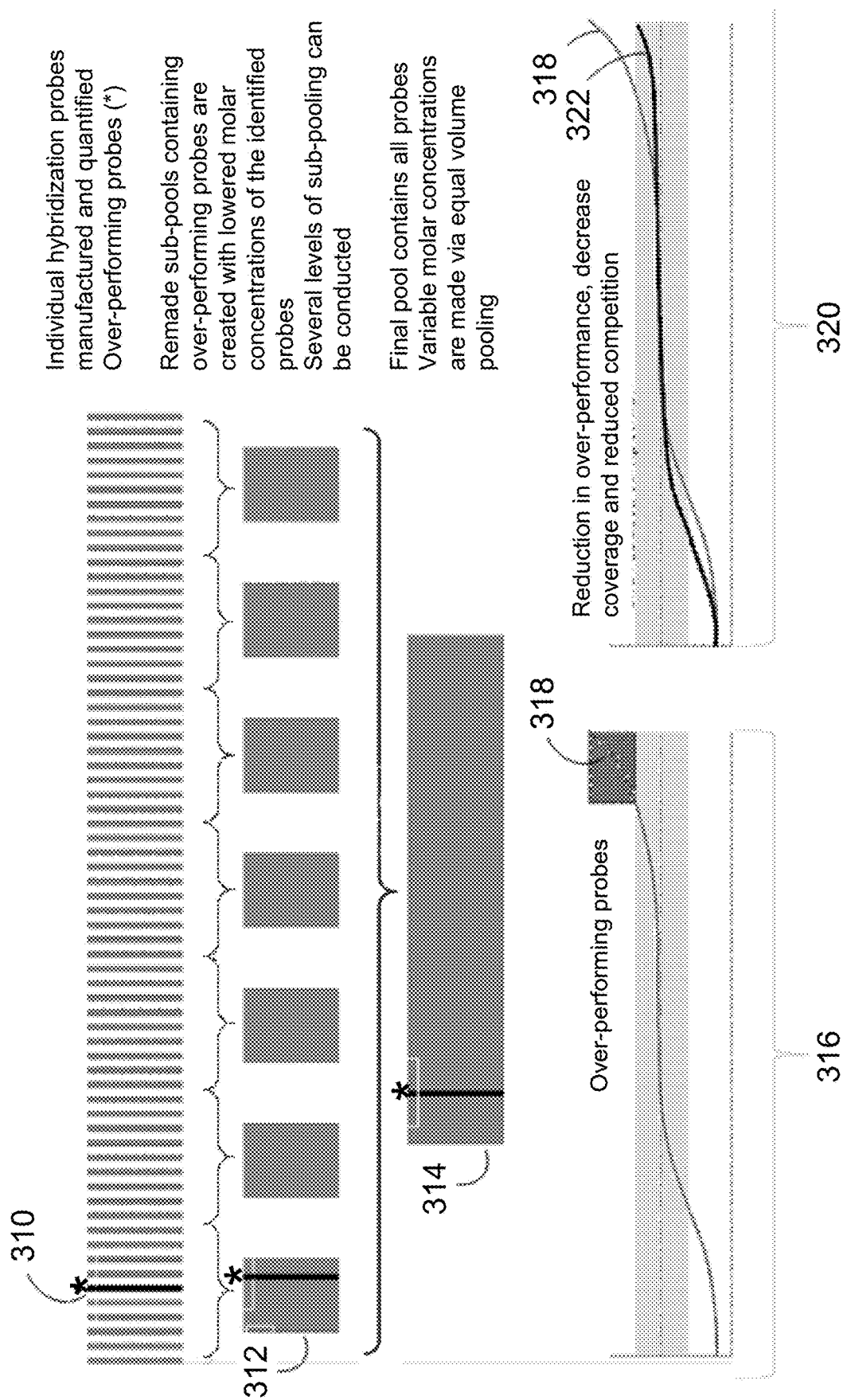

For example, as shown in FIG. 3B, one or more over-performing probes 310 are identified (e.g., these are those probes with coverage rates 318 that are higher than the tolerated range around the median coverage rate, as identified in the results from the first assay 316 of the set of probes against a sample). In some embodiments, each sub-pool (e.g., 312) including an over-performing probe can be remade to result in a lower concentration of said probe (e.g., each said sub-pool is reformulated to adjust the individual molarity of one or more probes). This enables reuse of the one or more sub-pools that do not include over-performing probes (e.g., sub-pools that do not include over-performing probes do not need to be remade).

Figure 3C:
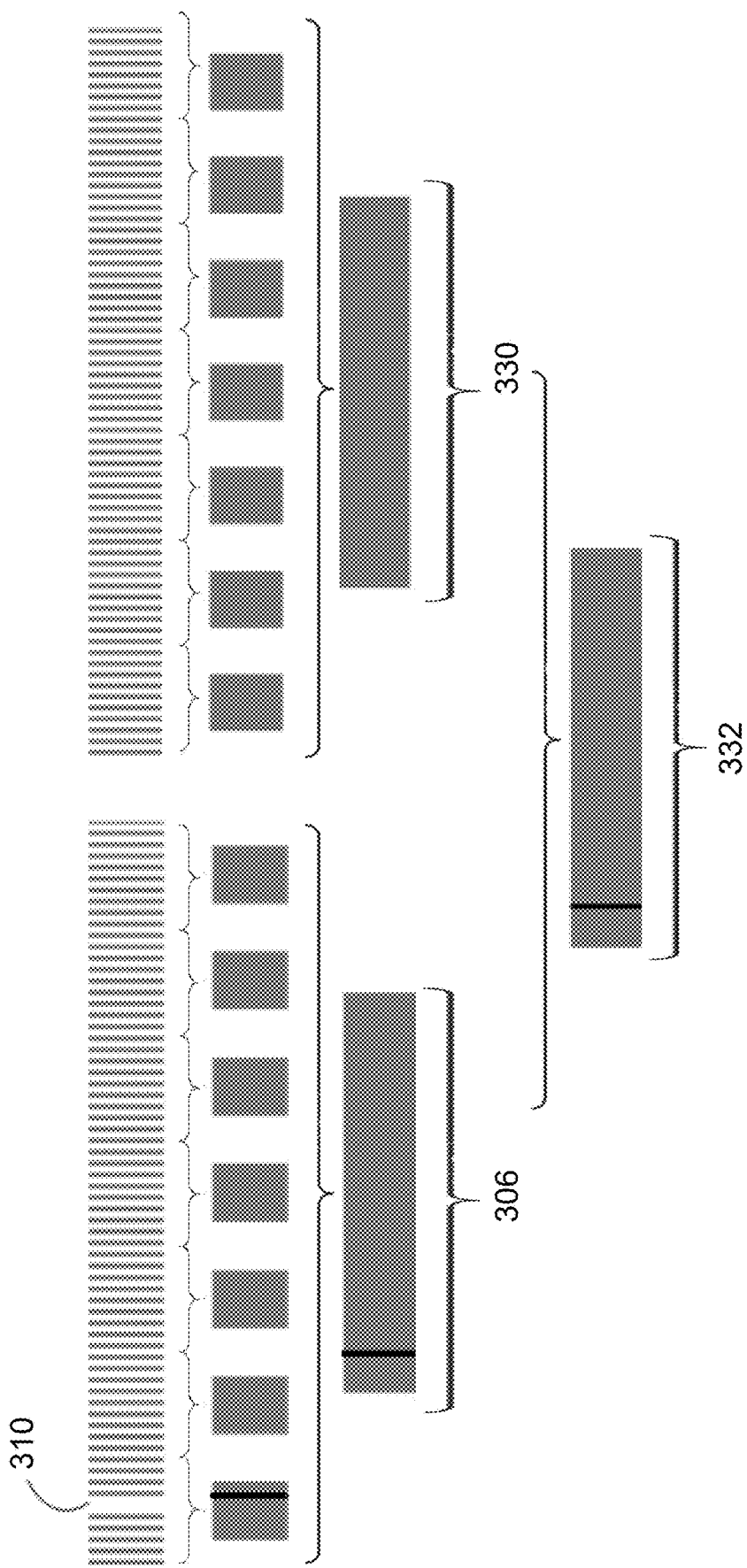

In some embodiments, the effective concentration of over-performing probes is reduced proportional to the detected recovery rate. In some embodiments, as shown in FIG. 3C, the effective concentration of one or more over-performing probes (e.g., 310) is reduced by adding the initial set of probes (e.g., 306) to a completely remade set of probes (e.g., 330) where the one or more over-performing probes have been excluded. This results in a final set of probes 332 where the concentration of one or more over-performing probes has been reduced based on the relative amounts of each of the component probe sets 306 and 330. For example, the effective concentration of each over-performing probe is reduced by at least 10%, by at least 20%, by at least 30%, by at least 40%, by at least 50%, by at least 60%, by at least 70%, by at least 80%, or by at least 90%.

In some embodiments, the effective concentration of one or more over-performing probes is reduced through suppression by competition. For example, in embodiments where the probes are labeled, the ratio of labeled to unlabeled probes can be altered (e.g., by reformulating one or more sub-pools that contain over-performing probes with unlabeled versions of said probes). In the art, such suppression is typically performed by adding a reverse complement of an over-performing probe to the set of probes; this reverse complement sequence then competes with the over-performing probe for hybridization with the target in the library.

Such methods may add complexity to the hybridization with patient sample. In particular, reverse complement sequences may interact with other probes in the probe set. Altering the labeled to unlabeled ratio of particular probes may have less of an effect on the function of the probe set. Further, the percentage of labeled probe may be directly proportional to the percentage of captured target, making this method more tunable and sensitive than previous methods in the art.

Block 212. Referring to block 212, in some embodiments, the method repeats the modifying and analyzing from blocks 208 and 210, respectively, until the respective updated recovery rate for each probe in the updated set of probes satisfies the predetermined recovery rate threshold, thereby providing the optimized set of probes for the sample library (e.g., the method reruns the modified assay). For example, the coverage of each probe in the updated probe set is quantified again in light of the alterations to the updated probe set. In some embodiments, probe performance is reevaluated after each adjustment of effective probe concentration (e.g., after each one of the steps taken to alter effective probe concentrations).

The remade final probe set, which is produced by combining the initial sub-pools and one or more remade sub-pools, can in some embodiments be assayed again against the sample library (e.g., see 320 in FIG. 3B). As can be seen in FIG. 3B by comparing the coverage rates of the original set of probes 324 with the coverage rates of the updated set of probes 322, the reduction in concentration of over-performing probes can result in reduced coverage of the previously over-performing probes.

Figure 3D:
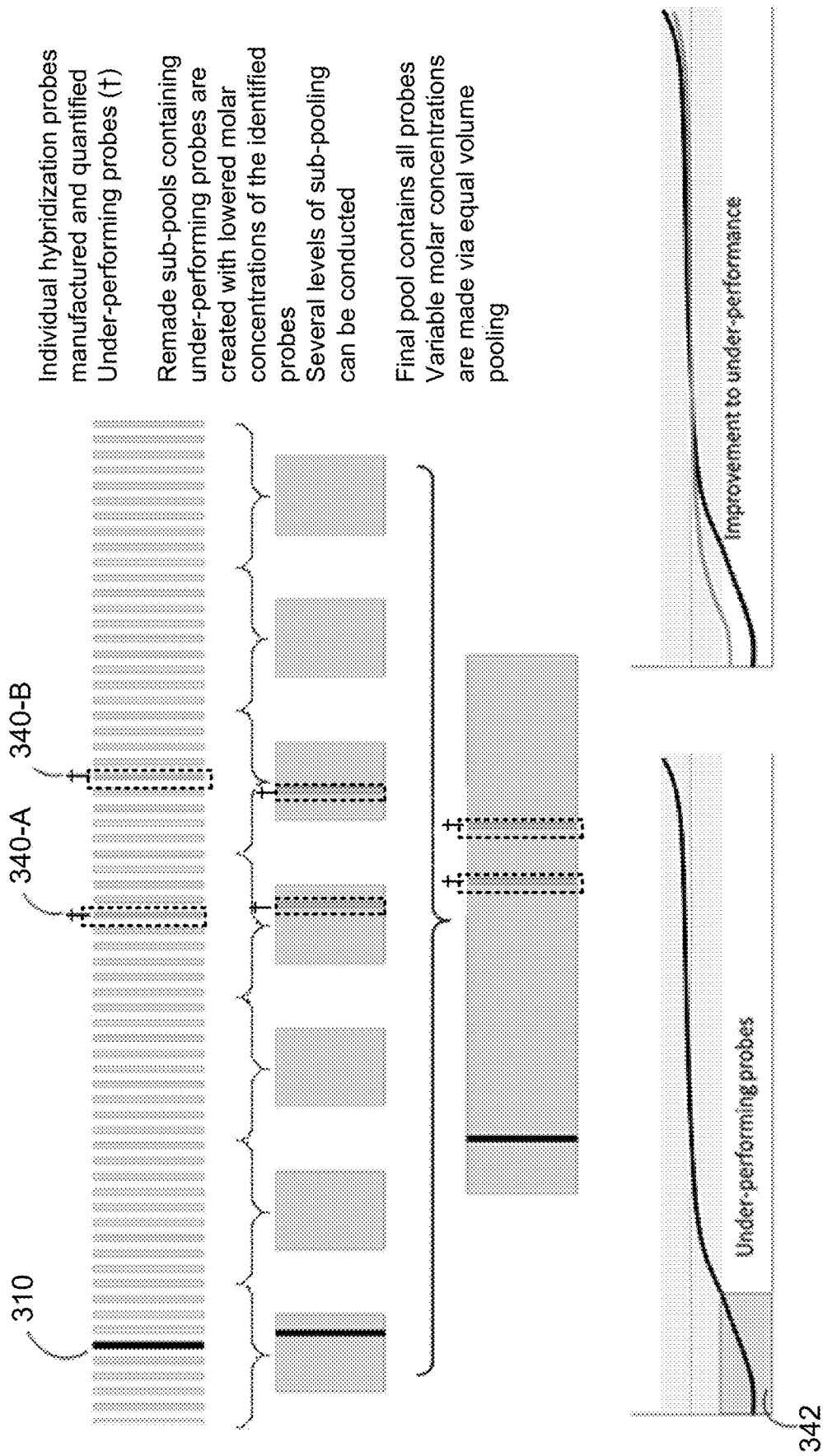
Figure 4:
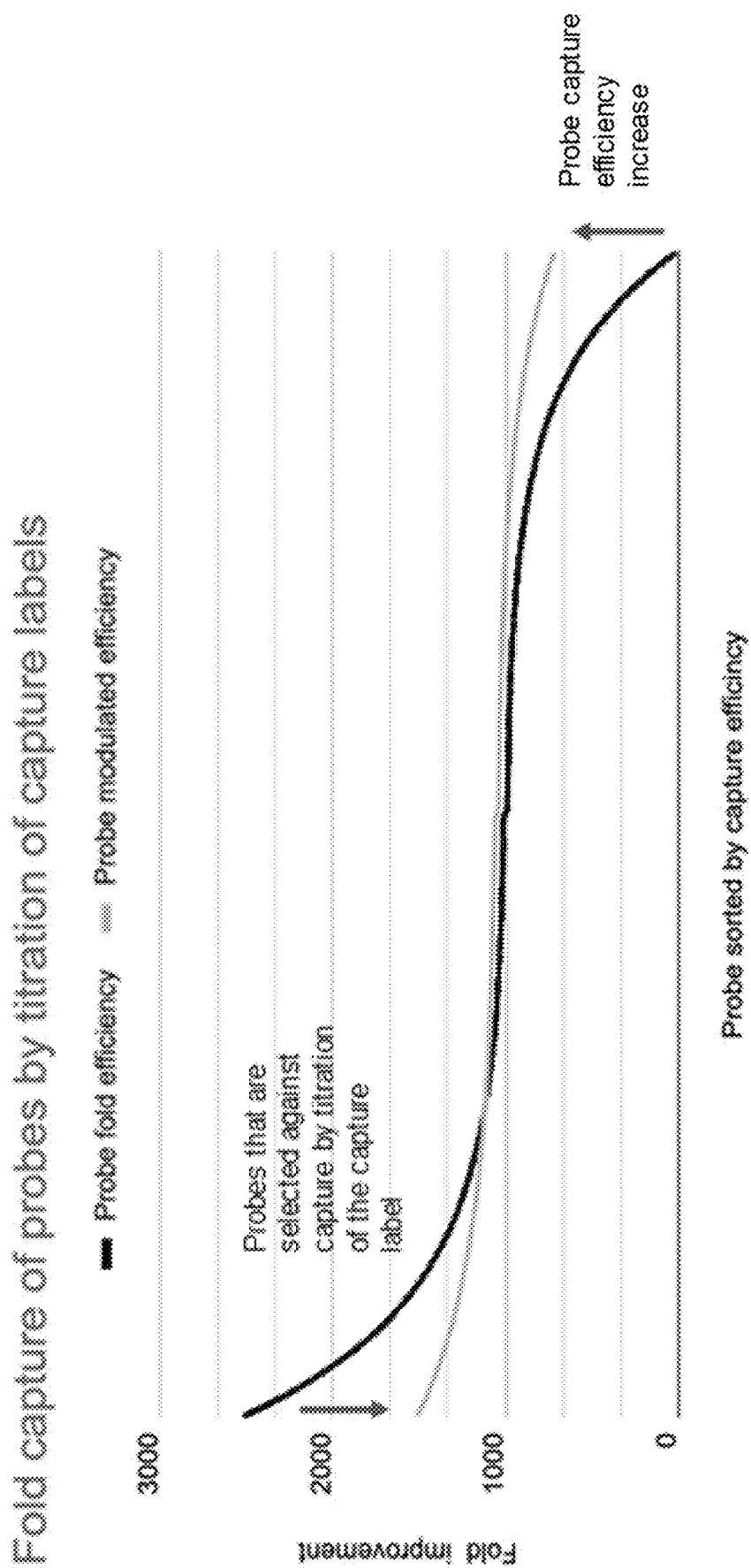
FIG. 4 illustrates an example of the improvement in the uniformity of sequencing coverage achieved using the optimized probe sets described herein, in accordance with some embodiments of the present disclosure.
Figure 5:
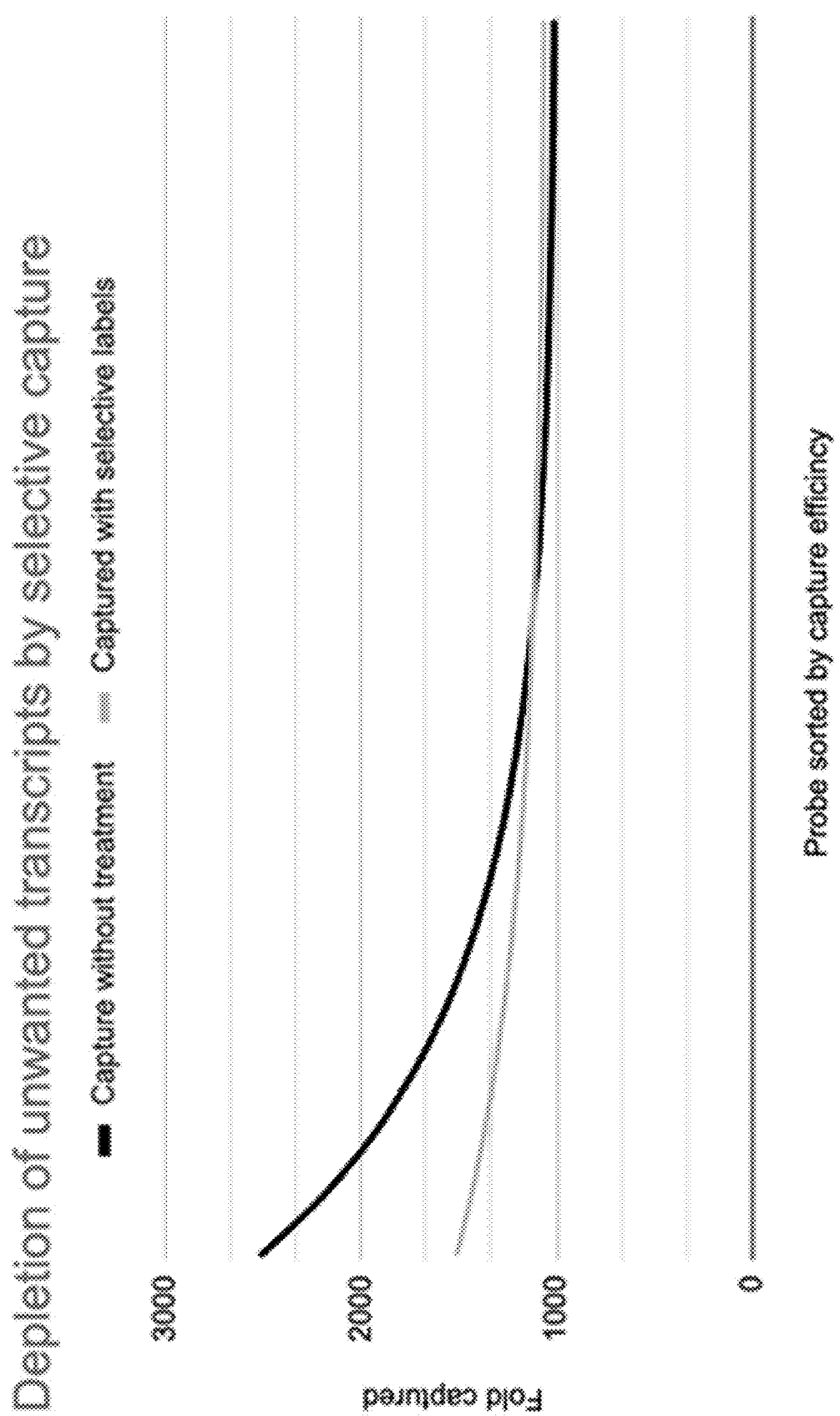
FIG. 5 illustrates an example of the improvement in the uniformity of sequencing coverage achieved by selectively depleting over-expressed transcripts in a sample, in accordance with some embodiments of the present disclosure. An example of selective capture that can be used on RNA transcripts that are overexpressed, for example, one or more of mitochondrial genes, ribosomal genes, globin genes, or host genes can be depleted to help detect infectious pathogen sequences, etc. Overexpressed gene transcripts may be removed from the pool using selective capture to reduce concentration in the sequencing pool, in accordance with some embodiments of the present disclosure.
Figure 6:
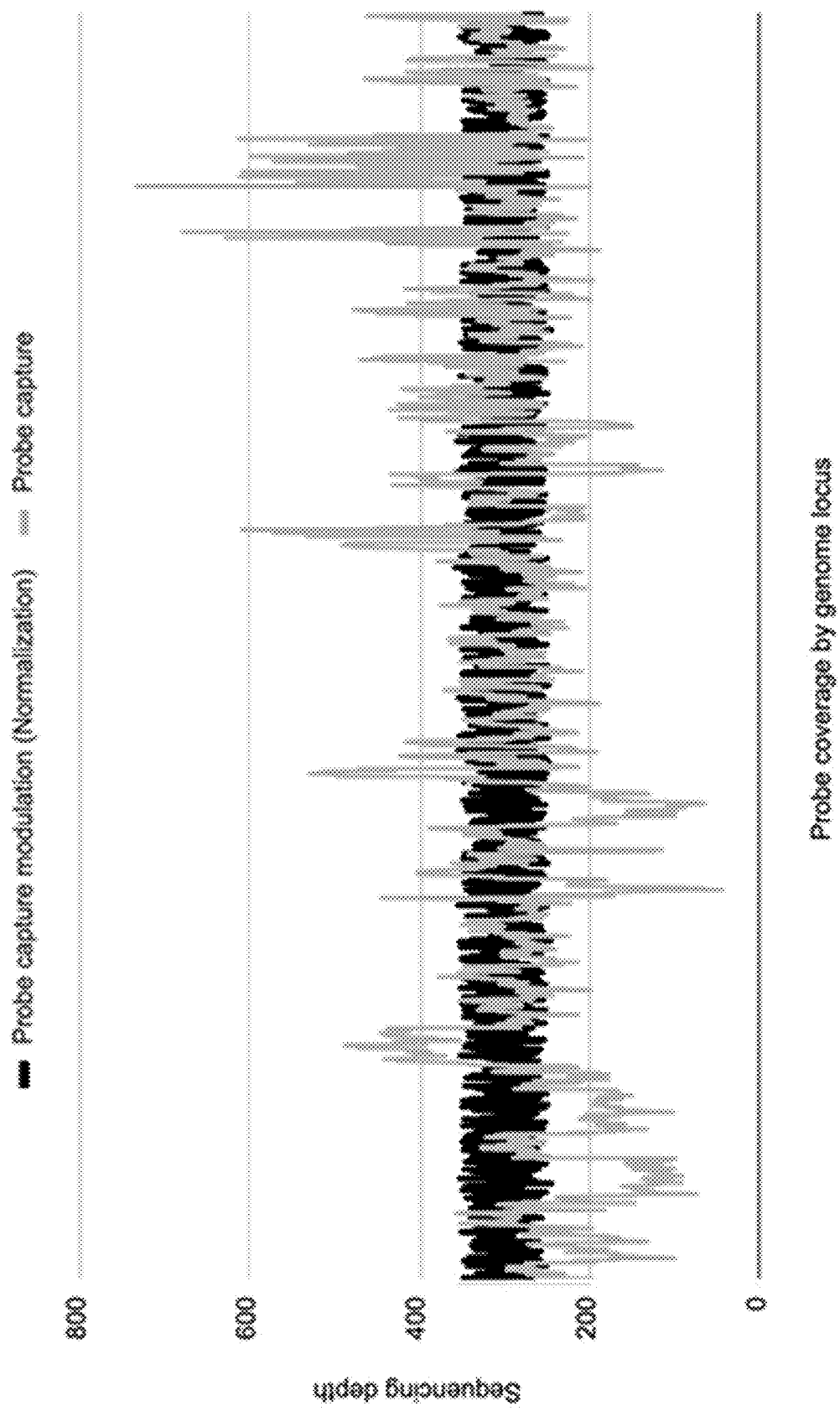
FIG. 6 illustrates an example of the improvement in the uniformity of sequencing coverage achieved using the optimized probe sets described herein, in accordance with some embodiments of the present disclosure. Variation in capture varies widely across the genome or target region. By balancing the capture labels on each probe the entire set can be tuned to more evenly distribute the capture efficiency across the genome or target region.

In some embodiments, the concentration of under-performing probes can be increased. Similar to the modulation of over-performing probes, one or more under-performing probes (e.g., those probes with capture rates 342 below the median capture rate) are identified as shown in FIG. 3D. In some embodiments, one or more sub-pools including one or more under-performing probes (e.g., 340-A and 340-B) can be reformulated to adjust the individual molarity of said under-performing probes.

Alternatively, similarly to FIG. 3C as described above, a second probe set (e.g., 330) is, in some embodiments, produced with either an increased molarity of under-performing probes or a decreased molarity of over-performing probes. By combining the redesigned probe set 330 with the first probe set 306 the concentration of under-performing probes can thus be increased.

In some embodiments, either under- or over-performing probes can be redesigned (e.g., by altering respective probe sequences) to alter binding affinities (e.g., to reduce the binding affinity of over-performing probes and/or to increase the binding affinity of under-performing probes).

In some embodiments, the method serves to optimize a probe set for a specific patient or a group of patients having a common characteristic (for example, a cohort of patients having the same cancer type or having the same variant). In such embodiments, the method proceeds by obtaining an initial set of probes; assaying the initial probe set against a sample of a specific patient; modifying the (effective) concentration of one or more selected probes to reduce the number of either over- or under-performing probes for the specific patient's sample; and rerunning the assay with the updated probe set. In such embodiments, as with other embodiments described herein, the modification and reanalysis steps are repeated as necessary until an optimal concentration of probes is achieved across a selected gene set. Such embodiments may be particularly useful for patients that will require multiple analyses (e.g., over time to monitor a health condition). In such circumstances, upon receipt of a subsequent sample from the specific patient, the assay can be rerun with the optimal concentration of probe sets. This aids in achieving standardized results for each patient and can help more accurately identify changes in a patient's results, leading to improved patient care and outcomes.

In some embodiments, where the probe set is optimized to a respective patient, the initial probe set is used to identify one or more nucleic acid (e.g., DNA or RNA) variants corresponding to said patient. In such embodiments, the initial probe set is then optimized using any method described herein to increase the effective concentration of probes that map to regions of interest (e.g., loci including an identified variant specific to the patient). In some embodiments, the concentration of probes that do not map to regions of interest (e.g., the negative backbone) is suppressed.

In some embodiments, optimizing a probe set for a specific cancer subtype requires using a sample library comprising one or more subject samples, where each subject has the specific cancer subtype.

In some embodiments, a method is provided for designing a uniform probe set. The method includes obtaining an initial set of probes, where each probe in the set of probes corresponds to a region of a reference genome, and each probe has a respective concentration. The method also includes analyzing the initial set of probes against a sample library, thereby obtaining at least i) a respective recovery rate for each probe in the initial set of probes, ii) a median recovery rate for the initial set of probes, and iii) a subset of probes, where the respective recovery rate of each probe in the subset of probes does not satisfy a predetermined recovery rate threshold. The method also includes modifying, for each probe in the subset of probes, the respective concentration of said probe, thereby obtaining an updated set of probes. The method also includes analyzing the updated set of probes against the sample library, thereby obtaining at least i) a respective updated recovery rate for each probe in the updated set of probes, ii) a median recovery rate for the updated set of probes, and iii) a subset of probes, where the respective recovery rate of each probe in the subset of probes does not satisfy a predetermined recovery rate threshold. The method then, optionally, includes repeating the modifying and analyzing until the respective updated recovery rate for each probe in the updated set of probes satisfies the predetermined recovery rate threshold, thereby providing the optimized set of probes for the sample library.

The embodiments described herein can be combined or used in any sequence as necessary to provide an optimized probe set suitable for a specific patient or for a particular assay (e.g., to assay for a mutation, specific cancer type, or other disease).

Improved Probe Sets

In some embodiments, the present disclosure provides improved probe sets that facilitate a more uniform nucleic acid capture and/or more uniform sequencing depth across one or more target regions of a genome. The advantageous properties of the probe sets described herein are derived, at least in part, by separately tuning the percentage of individual probe species that are conjugated to a capture moiety, such as biotin. In this fashion, by increasing the conjugation percentage of an under-performing probe species (i.e., a probe species that aligns to a genomic sequence that is represented, on average, at a much lower sequencing depth than other genomic sequences following nucleic acid capture), relative to the conjugation percentage of other probe species, the resulting probe set facilitates a more uniform sequencing depth for the entire probe set, e.g., by increasing the sequencing depth for the genomic sequence aligning to the under-performing probe species.

For example, in some embodiments, an optimized probe set composition is provided. The composition includes a first set of nucleic acid probes for determining a genomic characteristic (e.g., a single nucleotide variant (SNV), an indel, a copy number variation (CNV), a pseudogene, a CG-rich region, an AT-rich region, a genetic rearrangement, a splice variant, a gene expression level, aneuploidy, or chromosomal trisomy) of a first target region in a genome (e.g., an short genomic sequence, an exon, and intron, a plurality of contiguous exons, a plurality of contiguous exons and introns, a gene, a cluster of genes, tens to hundreds of contiguous kilobases of a chromosome, a chromosome arm, or an entire chromosome) of a subject.

The first set of nucleic acid probes includes a first plurality of nucleic acid probe species. Each respective nucleic acid probe species (e.g., all nucleic acid probes that align to the same subsequence of the target region) in the first plurality of nucleic acid probe species aligns to a different subsequence of the first target region of a reference genome for the species of the subject. For instance, in some embodiments, the first set of nucleic acid probes tile (e.g., overlapping or non-overlapping tiling) a genomic region, such as a gene. Thus, the nucleic acid probes in the set of probes bind to different subsequences of the genomic region.

As used herein, a "nucleic acid probe species" refers to all nucleic acid probes in a composition that align to the same or substantially the same genomic sequence (e.g., the first 150 nucleotides of a particular exon of a gene). Generally, all probes of a particular nucleic acid probe species will have the same nucleotide sequence. However, in some embodiments, a particular probe of nucleic acid probe species may have one or a small number of nucleotide variations relative to other probes within the nucleic acid probe species. For instance, in some embodiments, different probes of a first nucleic acid probe species may include either an A or a G (or any other combination of bases) at a particular position (e.g., nucleotide 78 of the probe). Regardless, two probes that differ by one or a small number of nucleotide variants still belong to the same nucleic acid probe species because they align to the same position in the genome. Similarly, it can be envisioned that, in some embodiments, a probe in a particular nucleic acid probe species may be one or a small number of nucleotides longer or shorter than other probes in the particular nucleic acid probe species. Similarly, it can be envisioned that, in some embodiments, a probe in a particular nucleic acid probe species may be shifted by one or a small number of nucleotides relative to the sequence of other probes in the particular nucleic acid probe species. For instance, in some embodiments, a first probe of a particular nucleic acid probe species may align to nucleotides 1-150 of an exon, while a second probe of the particular nucleic acid probe species may align to nucleotides 3-152 of the same exon. Regardless, two probes that are shifted by two nucleotides still belong to the same nucleic acid probe species because they align to the essentially the same position in the genome. Similarly, probes in a particular nucleic acid probe species may be differently conjugated to a chemical moiety. For instance, a first probe aligning to a particular genomic subsequence that is not chemically linked to a capture moiety (e.g., biotin) and a second probe aligning to the same particular genomic subsequence that is chemically linked to a capture moiety (e.g., biotin) still belong to the same nucleotide probe species because they align to the same position in the genome.

The composition includes, for each respective nucleic acid probe species in the first plurality of nucleic acid probe species, a first amount of a first version of the respective nucleic acid probe species that is conjugated to a capture moiety (e.g., biotin) and a second amount of a second version of the respective nucleic acid probe species that is not conjugated to a capture moiety. That is, a certain percentage of the probes that constitute the first nucleic acid probe species are conjugated to a capture moiety. Generally, the percentage of conjugated probes ranges from about 1% to about 100%, based upon how well the probe performs in a plurality of reference nucleic acid capture and sequencing assays (e.g., a training or diagnostic cohort of assays meant to establish a baseline performance for particular probe species). As such, when the genomic subsequence that the nucleic acid probe species aligns to is over-represented, on average, in the sequencing results of the reference assays (in the training set), a smaller percentage of that nucleic acid probe species will be conjugated to the capture moiety in the composition, e.g., to reduce the representation of the corresponding genomic sequence in the sequencing results. Likewise, when the genomic subsequence that the nucleic acid probe species aligns to is under-represented, on average, in the sequencing results of the reference assays (in the training set), a greater percentage of that nucleic acid probe species will be conjugated to the capture moiety in the composition, e.g., to increase the representation of the corresponding genomic sequence in the sequencing results. In this fashion, the improved probe set compositions described herein can be tuned to provide more uniform sequence coverage across of a genomic region and/or across multiple genomic regions (e.g., across multiple genes in a targeted panel, an entire exosome, or an entire genome). In some embodiments, this also allows for tuning sequencing coverage across one or more genomic regions without varying the molar concentration of particular nucleic acid probe sequences, which prevents certain pull-down biases caused by using different molar concentrations for different probes.

As such, within the composition there is a first ratio (e.g., a first percentage), for a first respective nucleic acid probe species in the first plurality of the nucleic acid probe species that aligns to a first subsequence of the first target region, of (i) the first amount of the first version of the first respective nucleic acid probe species to (ii) the second amount of the second version of the first respective nucleic acid probe species. For instance, 45% of the first nucleic acid probe species are conjugated to biotin. Similarly, within the composition, there is a second ratio (e.g., a second percentage), for a second respective nucleic acid probe species in the first plurality of the nucleic acid probe species that aligns to a second subsequence of the first target region, of (i) the first amount of the first version of the second respective nucleic acid probe species to (ii) the second amount of the second version of the second respective nucleic acid probe species. For instance, 60% of the second nucleic acid probe species are conjugated to biotin. Accordingly, the first ratio is different from the second ratio. That is, the percentage of probes aligning to one subsequence that are conjugated is different from the percentage of probes aligning to a different subsequence that are conjugated.

In some embodiments, the concentration of the first respective nucleic acid probe species in the first plurality of nucleic acid probe species is equal to the concentration of the second respective nucleic acid probe species in the first plurality of nucleic acid probe species. In some embodiments, the concentration of each respective nucleic acid probe species in the first set of nucleic acid probes is equal in the composition. That is, in some embodiments, each probe species corresponding to a target region (e.g., all probes used to tile a gene, a smaller genomic region, or a larger genomic region) is included in a nucleic acid capture and sequence assay at the same concentration. However, the percentage of each probe that is conjugated to a capture moiety differs, e.g., to account for differences in the performance of each capture probe. In this fashion, artifacts caused by biases resulting from using different concentrations of different probes are avoided.

As such, the improved probe compositions provided herein are tuned to improve the uniformity of sequence coverage across the target region. Accordingly, in some embodiments, when the composition is used in a reference nucleic acid capture and sequencing assay, the assay outputs an equal number of raw sequencing reads of the first subsequence of the first target region and the second subsequence of the first target region. The reference nucleic acid capture and sequencing assay refers to the particular assay, or a substantially similar assay, that was used to tune the conjugation percentages for the probe set composition. That is, in some embodiments, when the improved probe set compositions described herein are under the same assay conditions that were used to establish a baseline performance for nucleic acid probe species in the composition, the tuned compositions provide a more uniform sequence coverage for two or more (e.g., at least 10%, 15%, 25%, 30%, 40%, 50%, 60%, 70%, 80%, 90%, 95%, 99%, or 100%) of the genomic subsequences within the target region. In some embodiments, the sequence coverage for the two or more subsequences is within a 25%. In some embodiments, the sequence coverage for the two or more subsequences is within a 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.1%, or smaller range.

In some embodiments, the range of the first distribution becomes at least 5% more uniform across the gene, gene panel, target region, expression panels, whole or targeted exome, or whole genome in raw sequencing reads. In some embodiments, the range of the first distribution becomes at least 10%, 15%, 20%, 25%, 30%, 35%, 40%, 45%, 50%, 60%, 70%, 80%, 90%, 100%, 200%, 300%, or more uniform across the gene, gene panel, target region, expression panels, whole or targeted exome, or whole genome in raw sequencing reads Similarly, in some embodiments, when the composition is used in a reference nucleic acid capture and sequencing assay, the resulting sequence coverage between two or more (e.g., at least 10%, 15%, 25%, 30%, 40%, 50%, 60%, 70%, 80%, 90%, 95%, 99%, or 100%) of the genomic subsequences within the target region is improved by at least 25%, relative to the uniformity of the sequence coverage obtained when all of the probes are conjugated to the capture moiety at a same level (e.g., 100% or 50%). In some embodiments, the resulting sequence coverage between two or more of the genomic subsequences within the target region is improved by at least 30%, 40%, 50%, 60%, 70%, 80%, 90%1, 00%, 150%, 200%, 250%, 300%, 400%, 500%, 600%, 700%, 800%, 900%, or more.

According, in some embodiments, when the composition is used in a first reference nucleic acid capture and sequencing assay, the difference between (i) the number of raw sequencing reads output for the first subsequence of the first target region and (ii) the number of raw sequencing reads output for the second subsequence of the first target region (e.g., the variance in sequence coverage between the subsequences) is less than the difference between (iii) the number of raw sequencing reads output for the first subsequence of the first target region in a second reference nucleic acid capture and sequencing assay and (iv) the number of raw sequencing reads output for the second subsequence of the first target region in the second reference nucleic acid capture and sequencing assay, when the first reference nucleic acid capture and sequencing assay and the second reference nucleic acid capture and sequencing assay are performed using the same methodology, the second reference nucleic acid capture and sequencing assay is performed with a second composition including the first respective nucleic acid probe species and the second respective probe species, and in the second composition, the percentage of the first respective nucleic acid probe species that are conjugated to the capture moiety and the percentage of the second respective nucleic acid probe species that are conjugated to the capture moiety are the same.

In some embodiments, the difference between (i) the number of raw sequencing reads output for the first subsequence of the first target region and (ii) the number of raw sequencing reads output for the second subsequence of the first target region is at least 25% less than the difference between (iii) the number of raw sequencing reads output for the first subsequence of the first target region in the second reference nucleic acid capture and sequencing assay and (iv) the number of raw sequencing reads output for the second subsequence of the first target region in the second reference nucleic acid capture and sequencing assay. In some embodiments, the difference in the variance in the first reference assay is at least 30%, 40%, 50%, 60%, 70%, 80%, 90%, 100%, 150%, 200%, 250%, 300%, 400%, 500%, 600%, 700%, 800%, or 900 less than the variance in the second reference assay.

In some embodiments, when the composition is used in a reference nucleic acid capture and sequencing assay, the assay outputs for each respective nucleic acid probe species in the first plurality of nucleic acid probe species a corresponding number of raw sequence reads, thereby forming a first distribution of numbers of raw sequence reads for the respective subsequences of the first target region that align with a respective nucleic acid probe species in the first set of nucleic acid probes, and the range of the first distribution is less than 250% of the median of the distribution. In some embodiments, the range of the first distribution is less than 50% percent of the median of the distribution. In some embodiments, the range of the first distribution is less than 300%, 200%, 150%, 100%, 75%, 50%, 25%, or 10% percent of the median of the distribution.

Similarly, in some embodiments, when the composition is used in a reference nucleic acid capture and sequencing assay, the assay outputs for each respective nucleic acid probe species in the first plurality of nucleic acid probe species a corresponding number of raw sequence reads, thereby forming a first distribution of numbers of raw sequence reads for the respective subsequences of the first target region that align with a respective nucleic acid probe species in the first set of nucleic acid probes, and the first distribution has a fold-80 score of less than 1.5. As used herein, a "fold-80 score" is the fold of additional sequencing required to ensure that 80% of the target bases achieve the mean coverage. The lower the on-target rate, or the higher the fold-80 score, the greater the non-uniformity in sequence coverage across the target region. Accordingly, in some embodiments, the first distribution has a fold-80 score of less than 2, 1.9, 1.8, 1.75, 1.7, 1.6, 1.5, 1.4, 1.3, 1.25, 1.2, 1.15, 1.1, or 1.05.

In some embodiments, when the composition is used in a reference nucleic acid capture and sequencing assay, the assay outputs for each respective nucleic acid probe species in the first plurality of nucleic acid probe species a corresponding number of raw sequence reads, thereby forming a first distribution of numbers of raw sequence reads for the respective subsequences of the first target region that align with a respective nucleic acid probe species in the first set of nucleic acid probes, and the range of the first distribution is less than the range of a second distribution. The second distribution is determined by using a second composition in the reference nucleic acid capture and sequencing assay to output, for each respective nucleic acid probe species in the first plurality of nucleic acid probe species, a corresponding number of raw sequence reads, thereby forming the second distribution of numbers of raw sequence reads for the respective subsequences of the first target region that align with a respective nucleic acid probe species in the first set of nucleic acid probes, where in the second composition, the percentage of each respective nucleic acid probe species in the first plurality of nucleic acid probe species that are conjugated to the capture moiety is the same. In some embodiments, the range of the first distribution is at least 50% less than the range of the second distribution. In some embodiments, the range of the first distribution is at least 25%, 30%, 40%, 50%, 60%, 70%, 80%, 90%, 100%, 150%, 200%, 250%, 300%, 400%, 500%, 600%, 700%, 800%, or 900%, less than the range of the second distribution. In some embodiments, the fold-80 score of the first distribution is at least 50% less than the fold-80 score of the second distribution. In some embodiments, the fold-80 score of the first distribution is at least 25%, 30%, 40%, 50%, 60%, 70%, 80%, 90%, 100%, 150%, 200%, 250%, 300%, 400%, 500%, 600%, 700%, 800%, or 900 less than the fold-80 score of the second distribution.

In some embodiments, the first plurality of nucleic acid probe species is at least 10 nucleic acid probe species. In some embodiments, the first plurality of nucleic acid probe species is at least 5, 10, 15, 20, 25, 30, 40, 50, 75, 100, 200, 300, 400, 500, 750, 1000, 2500, 5000, 10,000, or more nucleic acid probe species.

In some embodiments, the first target region is a nucleotide, a portion of an intron, a portion of an exon, an intron, an exon, a subset of contiguous exons for a gene, a subset of contiguous exons and introns for a gene, a gene, a portion of a chromosome, an arm of a chromosome, or an entire chromosome.

In some embodiments, the first target region is a gene selected from the group consisting of BRCA1, BRCA2, a CYP gene, CYP2D, a PMS2 pseudogene, a PMSCL pseudogene, DMD, MET, TP53, ALK, IGF1, TLR9, FLT3, and a TCR/BCR gene.

In some embodiments, the capture moiety is biotin. In some embodiments, the capture moiety can be chemically modified to bind and hold or interfere with binding or lack of binding. Modulation of the kinetics of binding different probes with attach labels can be achieved with different affinities. Binding moieties are not limited in scope of association. In some embodiments, these could be covalent bonds, ionic bonding, polar covalent bonds, vander waal forces, hydrogen bonding, or electrostatic forces. These attached labels could include chemical alterations that affect the binding strength, alterations to the binding conditions, or alterations to the kinetics of the binding. Binding moieties could be modulated in concentration or type to affect selection of the desired probe. A plurality of binding moieties could be employed to modulate the effective capture of different groups of probes. The binding moieties could also be absent on the probe to modulate the effective population captured. Attached labels could also include a chemical cleavage group to modulate the effective capture of the probes. Examples of binding moieties include but are not limited to biotin:streptavidin, biotin:avidin, biotin:haba:streptavidin, antibody:antigen, antibody:antibody, covalent chemical linkage (e.g., click chemistry).

In some embodiments, the optimized probe composition also includes a second set of nucleic acid probes for identifying a genomic characteristic of a second target region in the genome of the subject. The second set of nucleic acid probes includes a second plurality of nucleic acid probe species. Each respective nucleic acid probe species in the second plurality of nucleic acid probe species aligns to a different subsequence of the second target region of the reference genome for the species of the subject. Accordingly, the composition includes, for each respective nucleic acid probe species in the second plurality of nucleic acid probe species, a first amount of a first version of the respective nucleic acid probe species that is conjugated to the capture moiety and a second amount of a second version of the respective nucleic acid probe species that is not conjugated to a capture moiety. As such, within the composition, there is a third ratio, for a first respective nucleic acid probe species in the second plurality of the nucleic acid probe species that aligns to a first subsequence of the second target region, of (i) the first amount of the first version of the first respective nucleic acid probe species to (ii) the second amount of the second version of the first respective nucleic acid probe species. Similarly, within the composition, there is a fourth ratio, for a second respective nucleic acid probe species in the second plurality of the nucleic acid probe species that aligns to a second subsequence of the second target region, of (i) the first amount of the first version of the second respective nucleic acid probe species to (ii) the second amount of the second version of the second respective nucleic acid probe species. Because the conjugation of the probe species is tuned to account for differences in probe efficiencies, the third ratio is different from the fourth ratio.

In some embodiments, the concentration of the first respective nucleic acid probe species in the second plurality of nucleic acid probe species is equal to the concentration of the second respective nucleic acid probe species in the second plurality of nucleic acid probe species. In some embodiments, the concentration of each respective nucleic acid probe species in the second set of nucleic acid probes is equal in the composition. That is, in some embodiments, each probe species corresponding to a target region (e.g., all probes used to tile a gene, a smaller genomic region, or a larger genomic region) is included in a nucleic acid capture and sequence assay at the same concentration. However, the percentage of each probe that is conjugated to a capture moiety differs, e.g., to account for differences in the performance of each capture probe. In this fashion, artifacts caused by biases resulting from using different concentrations of different probes are avoided.

In some embodiments, the concentration of the first respective nucleic acid probe species in the second plurality of nucleic acid probe species is equal to the concentration of the first respective nucleic acid probe species in the first plurality of nucleic acid probe species. In some embodiments, the concentration of each respective nucleic acid probe species in the second set of nucleic acid probes is equal to the concentration of each respective nucleic acid probe species in the first set of nucleic acid probes in the composition. That is, in some embodiments, the concentrations of probes to two or more different genomic regions (e.g., two or more genes in a targeted gene panel, two or more genes in a whole exosome, or two or more genomic regions in a whole genome) are the same within the composition. In some embodiments, all of the probes in the composition are at the same concentration.

As described above with reference to the first set of nucleic acid probes, in some embodiments, when the composition is used in a reference nucleic acid capture and sequencing assay, the assay outputs an equal number of raw sequencing reads of the first subsequence of the second target region and the second subsequence of the second target region.

In some embodiments, the first ratio is different from the third ratio and the fourth ratio. That is, in some embodiments, the percentage of conjugated probes for a probe species in the first set of probes is different from the ratio of conjugated probes for two or more of the probe sequences in the second set of probes. In some embodiments, the second ratio is different from the third ratio and the fourth ratio.

In some embodiments, when the composition is used in a reference nucleic acid capture and sequencing assay, the assay outputs an equal number of raw sequencing reads of the first subsequence of the first target region and the first subsequence of the second target region.

In some embodiments, the concentration of each respective nucleic acid probe species in the second set of nucleic acid probes is equal in the composition.

In some embodiments, when the composition is used in a reference nucleic acid capture and sequencing assay, the assay outputs for each respective nucleic acid probe species in the second plurality of nucleic acid probe species a corresponding number of raw sequence reads, thereby forming a second distribution of numbers of raw sequence reads for the respective subsequences of the second target region that align with a respective nucleic acid probe species in the second set of nucleic acid probes, and the range of the second distribution is less than 250% of the median of the distribution. In some embodiments, the range of the second distribution is less than 50% percent of the median of the distribution. In some embodiments, the range of the second distribution is less than 300%, 200%, 150%, 100%, 75%, 50%, 25%, or 10% percent of the median of the distribution.

In some embodiments, when the composition is used in a reference nucleic acid capture and sequencing assay, the assay outputs for each respective nucleic acid probe species in the second plurality of nucleic acid probe species a corresponding number of raw sequence reads, thereby forming a second distribution of numbers of raw sequence reads for the respective subsequences of the second target region that align with a respective nucleic acid probe species in the second set of nucleic acid probes, and the second distribution has a fold-80 score of less than 1.5. In in some embodiments, the second distribution has a fold-80 score of less than 2, 1.9, 1.8, 1.75, 1.7, 1.6, 1.5, 1.4, 1.3, 1.25, 1.2, 1.15, 1.1, or 1.05.

In some embodiments, the second plurality of nucleic acid probe species is at least 10 nucleic acid probe species. Ins some embodiments, the second plurality of nucleic acid probe species is at least 5, 10, 15, 20, 25, 30, 40, 50, 75, 100, 200, 300, 400, 500, 750, 1000, 2500, 5000, 10,000, or more nucleic acid probe species.

In some embodiments, the first target region is a gene selected from BRCA1, BRCA2, a CYP gene, CYP2D, a PMS2 pseudogene, a PMSCL pseudogene, DMD, MET, TP53, ALK, IGF1, TLR9, FLT3, and a TCR/BCR gene.

In some embodiments, a method is provided for determining a genomic characteristic of a subject. The method includes contacting a sample comprising nucleic acids from the subject with an optimized probe composition as described herein. The method also includes recovering a portion of the nucleic acids using an agent that binds to the capture moiety, and sequencing the recovered portion of the nucleic acids, thereby identifying a genomic characteristic of the subject.

In some embodiments, the genomic characteristic includes a single nucleotide variant (SNV), an indel, a copy number variation (CNV), a pseudogene, a CG-rich region, an AT-rich region, a genetic rearrangement, a splice variant, a gene expression level, aneuploidy, or a chromosomal trisomy.

In some embodiments, the nucleic acids from the subject are obtained from a liquid biological sample from the subject. In some embodiments, the liquid biological sample is a blood sample or a blood plasma sample from the subject. In some embodiments, the nucleic acids from the subject are obtained from a solid biological sample from the subject. In some embodiments, the solid biological sample is a tumor sample or a normal tissue sample from the subject.

In some embodiments, the nucleic acids include mRNA or cDNA generated from mRNA, and the method also includes, prior to contacting the sample with the composition, selectively removing a portion of the mRNA or cDNA from a first gene that is represented in the sample at a level that is greater than the representation of at least 50% of the genes represented in the sample. In some embodiments, the first gene is represented in the sample at a level that is greater than the representation of at least 75% of the genes represented in the sample. In some embodiments, the first gene is represented in the sample at a level that is greater than the representation of at least 55%, 60%, 65%, 70%, 75%, 80%, 85%, 90%, or 95% of the genes represented in the sample.

In some embodiments, a method is provided for determining a genomic characteristic of a subject. The method includes identifying a first genomic characteristic of the subject from a first sample including nucleic acids from the subject by: contacting the first sample comprising nucleic acids from the subject with a first optimized probe composition as described herein, recovering a portion of the nucleic acids from the first sample using an agent that binds to the capture moiety, and sequencing the portion of the nucleic acids recovered from the first sample. The method includes identifying a second genomic characteristic of the subject from a second sample comprising nucleic acids from the subject by: contacting the second sample comprising nucleic acids from the subject with a second optimized probe composition as described herein, recovering a portion of the nucleic acids from the second sample using an agent that binds to the capture moiety, and sequencing the portion of the nucleic acids recovered from the second sample. The first set of nucleic acid probes in the first composition and the first set of nucleic acid probes in the second composition align to the same target region of the reference genome for the species of the subject. The first respective nucleic acid probe species in the first plurality of the nucleic acid probe species in the first composition and the first respective nucleic acid probe species in the first plurality of the nucleic acid probe species in the second composition align to the same subsequence of the same target region. The first ratio for the first respective nucleic acid probe species in the first plurality of the nucleic acid probe species in the first composition is different than the first ratio for the first respective nucleic acid probe species in the first plurality of the nucleic acid probe species in the second composition.

In some embodiments, the nucleic acids in the first sample are obtained from a biological sample from a first tissue in the subject and the nucleic acids in the second sample are obtained from a biological sample obtained from a second tissue in the subject. In some embodiments, the nucleic acids in the first sample are obtained from a solid biological sample from the subject and the nucleic acids in the second sample are obtained from a liquid biological sample from the subject. In some embodiments, the solid biological sample is a tumor sample or a normal tissue sample from the subject. In some embodiments, the liquid biological sample is a blood sample or a blood plasma sample from the subject. In some embodiments, the nucleic acids in the first sample are DNA and the nucleic acids in the second sample are RNA.

In some embodiments, the nucleic acids in the first sample represent a whole exome from the subject and the nucleic acids in the second sample represent a targeted panel of nucleic acid sequences from the subject.

EXAMPLES

BRCA1 and BRCA2 are genes that are known to have a prevalence of large INDEL (insertion/deletion) variants that are clinically relevant. For example, the presence of an INDEL variant in the BRCA1 or BRCA2 gene in a germline/non-cancerous specimen from a patient may be associated with a particular risk for developing breast cancer. For example, the presence of an INDEL variant in the BRCA1 or BRCA2 gene in a somatic/cancer specimen from a patient may be associated with a particular prognosis, diagnosis, and/or matching therapy likely to be effective in slowing the progression of the patient's cancer.

However, large INDELs can be difficult to detect by next generation sequencing (NGS) because of the nature of short read sequencing by synthesis NGS technology. In this example, the systems and methods may be used to more uniformly sequence a BRCA gene (for example, resulting in similar numbers of sequencing reads associated with each region targeted by a probe during hybridization capture), which may facilitate the detection of INDEL variants in the BRCA gene.

In this example, the systems and methods receive a genetic sequence associated with a human BRCA gene. The sequence may be received from a database such as the National Center for Biotechnology Information (NCBI) or a similar database of genetic sequences. This example may apply to the BRCA 1 and/or BRCA 2 gene.

The genetic sequence may be annotated or the systems and methods may annotate the genetic sequence. Annotation may include labeling portions of the genetic sequence as a start sequence, promoter region(s), another class of genetic region, etc.

The systems and methods may design a plurality of probes or receive a set of BRCA1 or BRCA2 probes (for example, probes for hybridization capture, for example, for use during library generation for next generation sequencing) and each probe may target a distinct genetic locus associated with the BRCA1 or BRCA2 gene. The regions targeted by probes may be spaced uniformly across the BRCA1 or BRCA2 gene (for example, having approximately the same number of bases between each target), or the regions targeted by probes may be concentrated in certain regions of the BRCA1 or BRCA2 gene. As an example, a high density of probes designed toward a target region could be needed due to a high prevalence of known recurring genetic mutations in that region (for example, the region may be a hotspot). In another example, a high density of probes designed toward a target region could be needed due to unfavorable hybridization kinetics or specificity of probes that target that region. Target regions may all be located in exon regions, intron regions, promoter regions, or any combination thereof. It is also possible to include regularly spaced probes at any spacing (for example, 1 probe per 10 kB, 100 KB, 1 MB, etc.), which may be done throughout an entire genome or a portion of the genome. In one example, each probe is 120 base pairs long.

Probes covering the BRCA genes could be designed as one probe per exon or multiple probes per exon that could be tiled end-to-end (for example, the nucleotide targeted by the end of one probe is adjacent to a nucleotide targeted by the neighboring probe, but there are no nucleotides targeted by both a probe and a neighboring probe), overlap (for example, one or more adjacent nucleotides may be targeted by more than one probe), or spaced apart (for example, there may be untargeted nucleotides between the nucleotides targeted by a first probe and the nucleotides targeted by a second probe). Probes covering the BRCA genes could also include probes targeting the intronic regions. Intronic probes could include a single probe per intron or multiple probes per intron that are regularly or irregularly spaced. Probes covering the BRCA genes could also include probes targeting the promoter regions of the genes with one or multiple probes. Probes could also be designed and included to target intergenic regions neighboring the BRCA genes with one or multiple probes.

Probe design may be fully manual, or partially or entirely automated through the use of a probe design software program.

The plurality of probes may be used during the generation of a sequencing library (for example, for enrichment for next generation sequencing) from one or more test specimens or control samples known to comprise a BRCA region in order to confirm that the plurality of probes align to the relevant target regions in the BRCA gene. In another embodiment, testing may be accomplished using in silico methods, which may include the use of probe design software.

The probe design may account for unique aspects of the BRCA gene. For instance, certain regions of the BRCA gene are expected to contain large deletions and/or duplications (for example, INDEL variants) that span a portion of an exon or an intron, are approximately 1 kilobase or larger in size, span one or more exons and/or introns, or may be of varying sizes (for example, INDELs caused by alu insertions). For an example of BRCA1 or BRCA2 INDELs, see Schmidt A Y et al, J Mol Diagn., 19(6):809-16 (2017), the contents of which are incorporated by reference herein in their entirety. As another example, probes may be designed to provide coverage across exonic regions of the BRCA gene, intronic regions of the BRCA gene, or both exon and intron regions of the BRCA gene.

The probes may be tested and adjusted to achieve even sequencing coverage across the entire BRCA1 or BRCA2 gene, including promoter(s), exons, and introns (for example, each probe may be adjusted such that next generation sequencing results in approximately the same number of sequencing reads mapping to each region targeted by a probe).

In order to compare the number of reads associated with each target region, a sequencing library may be prepared from one or more test specimens or control samples known to comprise a wildtype or normal BRCA gene, using the plurality of probes. In one example, the test specimen is a solid specimen (for example, a tumor biopsy, an FFPE tissue section, etc.). In another example, the test specimen is a liquid specimen (for example, a blood specimen, a liquid biopsy specimen, etc.).

For each probe, multiple copies (molecules) of the probe may be used for hybridization and capture during library generation. Each individual probe molecule may or may not be biotinylated or labeled by another labeling molecule. For each probe, the proportion or percentage of individual probe molecules that are labeled (for example, biotinylated) may be known and adjusted. The concentration of each probe may be measured (for example, in molarity units, or other similar units used for measuring the concentration of a molecule). In one example, each probe is added in an amount of approximately 0.1 to 100 picomolar (pM). For each probe, the concentration may be adjusted.

For each probe, the systems and methods may adjust the percentage of the individual probe molecules that are biotinylated, for example, based on the coverage calculated for each probe (for example, the number of reads associated with each target region). For instance, the biotinylation percentage of each probe that targets the BRCA gene may be adjusted depending on the number of reads from that probe in comparison to reads of other probes targeting other loci in the BRCA gene. As another example, the biotinylation percentage of each probe in the plurality of probes may be adjusted depending on the number of reads from that probe in comparison to reads of other regions in the BRCA gene. In some embodiments, more than one probe may be responsible for producing reads for a region.

Row 1 in Table 1 shows the number of reads associated with each of five hypothetical probes targeting the BRCA gene, where each probe is 100% biotinylated. The third row shows the new biotinylation percentages (33.2, 91.1, 26.9, 34.4, and 56.5%), selected based on the number of reads associated with each probe. In this example, the new biotinylation percentages should result in each probe being associated with approximately 71 reads (approximately the same percentage of the total reads). Other biotinylation percentages could be selected such that each probe is associated with an approximately equal number of reads. For example, 16.6, 45.5, 13.4, 17.2, and 28.2% may result in each probe being associated with approximately 71 reads.

The biotinylation percentages may be adjusted for each probe and tested to determine the number of reads associated with each probe at the new biotinylation percentage. If the number of reads associated with each probe is highly variable, the biotinylation percentage may be adjusted again. These steps may be repeated multiple times, for example, until the number of reads associated with each probe is less variable.

Five probes are shown in this example, but in reality 1,000, 10,000, 100,000 or more probes may be used to cover the BRCA gene and a new biotinylation percentage may be calculated and tested for each probe.

In various embodiments, having an approximately equal number of reads associated with each target region may facilitate the detection of duplications and/or deletions (IN-DELs) in a BRCA gene, for example, in a specimen having a BRCA gene that has deletions, duplications, or is otherwise not wildtype or not normal.

TABLE 1

|  | Probe 1 | Probe 2 | Probe 3 | Probe 4 | Probe 5 | Combined Total Reads |
| --- | --- | --- | --- | --- | --- | --- |
| No. of reads | 85 | 31 | 105 | 82 | 50 | 353 |
| Percent of total Reads | 24.1% | 8.8% | 29.7% | 23.2% | 14.2% | 100.0% |
| New biotinylated | 0.332 | 0.911 | 0.269 | 0.344 | 0.565 |  |
| New Percent activity | 20.0% | 20.0% | 20.0% | 20.0% | 20.0% |  |
| Predicted total reads | 71 | 71 | 71 | 71 | 71 | 353 |

After the biotinylation percentage is adjusted for each probe, such that the number of reads associated with each probe is approximately equal, the systems and methods may compare the number of reads associated with the entire BRCA gene to the number of reads associated with each of a plurality of additional genes selected from a targeted sequencing panel.

The systems and methods may adjust the concentration of the BRCA gene probes based on the number of reads associated with each selected gene in the sequencing panel. The concentration of the BRCA gene probes may be adjusted in an attempt to have approximately the same number of BRCA gene reads as the number of reads associated with each gene selected for the comparison. Methods other than concentration adjustment may be used. For example, the proportion of probe molecules having capture moieties may be reduced for all probes targeting genes associated with a large number of reads.

Table 2 illustrates the concept of altering the concentration of a probe or pool of multiple probes to attempt to achieve more uniform coverage. Historically, adjusting the concentrations of probes does not always result in a predictable change in hybridization kinetics and may have other off target effects.

Table 2 shows the number of reads associated with each of four hypothetical genes and the BRCA gene, where the plurality of probes associated with each gene have a measurable concentration. The third row shows the factor by which the original concentration may be multiplied to generate a new concentration such that all genes have approximately 730 reads. Other concentration adjustment factor values could be selected such that each gene is associated with an approximately equal number of reads. For example, 0.930×, 1.916×, 0.606×, 0.881×, and 1.622×may result in each gene being associated with approximately 730 reads.

Five genes are shown in this example, but in reality 20,000 genes, or hundreds of thousands of alleles or transcripts of genes may be included in a targeted sequencing panel and a concentration adjustment factor may be calculated for each one.

The concentrations may be adjusted for each probe set (for each gene) and tested to determine the number of reads associated with each gene at the new concentration. If the number of reads associated with each gene is highly variable, the concentration may be adjusted again. These steps may be repeated multiple times, for example, until the number of reads associated with each gene is less variable.

Additional concentration adjustments may include: increasing the concentration(s) of vastly underperforming probe(s) (for example, probes that are associated with a lower number of reads), and/or establishing multi-tiered coverages (for example, instead of the entire genome having a uniform coverage, a first region of the genome may have a first coverage, a second region of the genome may have a second coverage, a third region of the genome may have a third coverage, etc.). To illustrate an example of multi-tiered coverage, the BRCA1 or BRCA2 gene may have a coverage of 500× and the rest of the panel may have a coverage of 150×. In alternative embodiments, any gene of interest or gene that is difficult to sequence may have a coverage that is higher than other portions of a genome. For example, a gene of interest may have a coverage of 10,000×.

TABLE 2

| | BRCA gene | Gene 2 | Gene 3 | Gene 4 | Gene 5 |
|---|---|---|---|---|---|
| No. of reads | 785 | 381 | 1205 | 829 | 450 |
| Concentration adjustment factor | 0.465 | 0.958 | 0.302 | 0.440 | 0.811 |

The systems and methods may report any detected INDEL variants in the BRCA1 or BRCA2 gene of a patient specimen to a geneticist or medical professional in order to aid the professional in counseling or treating the patient.

The systems and methods may apply the concepts of biotinylation percentage adjustments, concentration adjustments, and other adjustments to affect probe performance (for example, to achieve uniform coverage across a genetic region) in additional use cases other than detecting INDEL variants in the BRCA1 or BRCA2 gene. In one example, the systems and methods are used to generate more uniform coverage of a TP53 gene.

For example, the systems and methods may be used to achieve uniform coverage of a CYP gene (for example, CYP2D6) to facilitate the detection of reads from CYP pseudogenes, rearrangements, INDEL variants and/or copy number variants (CNVs) in the CYP gene. If the systems and methods detect CYP gene variants or other CYP gene-related data in a patient specimen, the systems and methods may inform a physician, medical professional, or geneticist about the variant or data and any known or predicted effects that the variant(s) or data may have on the patient's RNA expression levels (for example, for a CYP gene, for each allele of a CYP gene) and/or drug metabolism rate.

The systems and methods may be used to facilitate determining if a sequencing read is associated with a pseudogene to prevent inaccurately aligning a pseudogene read to a gene having a sequence that is similar to the pseudogene.

In one example, the systems and methods may optimize a probe set to achieve more even coverage of the PMS2 gene and/or PMSCL pseudogene to facilitate the accurate alignment of sequencing reads to either the PMS2 gene or the PMSCL pseudogene. Certain, known variants in the PMS2 gene are associated with an increased risk for multiple cancer types (for example, colorectal, endometrial, ovarian, stomach, urinary cancer, etc.) If a PMS2 variant is detected by NGS without the use of an optimized probe set, it may be difficult to be certain that the variant is in PMS2 and not in the PMSCL pseudogene. If the systems and methods detect a PMS2 variant associated with increased risk for developing cancer, the systems and methods may inform a patient, physician, medical professional, or geneticist of the presence of the PMS2 variant in the patient.

In one example, the systems and methods may optimize a probe set to facilitate the detection of exon skipping, splice variants, alternative splicing, or differential splicing of a gene with the use of NGS or RNA-seq. In various embodiments, splice variants could be generated by fusion events, splice sites, mutations in genes encoding for splice factors, etc. Exon skipping may be difficult to detect by DNA-seq.

In one example, the systems and methods may optimize a probe set to generate more uniform coverage of the DMD gene. The DMD gene is very large (at least 2,300 kb long) and has approximately 80 exons. There are many splice variants (for example, skipped exons) for this gene, and more uniform coverage of the gene transcripts would facilitate detection of splice variants. In some examples, the splice variant is an inherited germline variant. In some examples, exon skipping in the DMD gene has clinical relevance for Duchenne muscular dystrophy. For example, exon skipping in an mRNA transcript of the DMD gene may prevent ribosomes from translating the DMD mRNA into dystrophin protein, exacerbating the muscular dystrophy. For patients with a particular skipped exon, a treatment (for example, eteplirsen) may be recommended to induce production of dystrophin protein (often a shortened version of the protein) from DMD mRNA missing certain exons. The systems and methods may report detected DMD variants and any prognosis, diagnosis, and/or matched therapy associated with the detected variants.

In another example, the systems and methods optimize probes for detecting exon skipping in the MET gene (for example, MET Exon 14 skipping). In various embodiments, if exon 14 of MET gene is spliced (skipped), the cell is more active or oncogenic. For example, cancer cells may have exon 14 skipped as a somatic mutation, especially non-small cell lung cancer (NSCLC). Patients having a MET splice variant may respond favorably (for example, showing a slowed progression of cancer or disease) to treatment with MET targeted therapies (for example, capmatinib, crizotinib, pembrolizumab, MET tyrosine kinase inhibitors, etc.) For an example of therapies and trials targeting MET splice variants, see Reungwetwattanaa T. et al, Lung Cancer, 103:27-37 (27), the content of which is incorporated herein in its entirety for all purposes. The systems and methods may report any detected MET splice variants and any prognosis, diagnosis, and/or matched therapy associated with the detected MET splice variants.

In one example, the systems and methods may optimize a probe set to facilitate the detection of fusions (for example, RNA fusions) with the use of NGS.

In one example, the ALK gene can form fusions with a variety of partner genes, especially in cancer cells (for example, NSCLC). This variety of genes that can partner with ALK gives rise to a variety of fusion variants, many of which have not been previously characterized by scientific research publications. One example of a partner gene is EML4. In an EML4-ALK fusion, EML4 expression is driving the ALK expression. (In various embodiments, any gene could be the partner gene).

The fusion variant could cause differential expression on the 3' side of the ALK gene vs the 5' side of the ALK gene. For example, the systems and methods may facilitate the detection of non-equal expression levels of ALK exon 1 and the final exon of ALK. This information may indicate the presence of a fusion variant. The systems and methods may also improve the uniformity of coverage at each exon of ALK, to facilitate locating which exon in ALK contains the fusion breakpoint.

In various examples, exon 20 in the ALK gene is a common breakpoint. If a fusion formed with the 3' side of a partner gene and the 5' side of the ALK gene (starting in exon 20 of the ALK gene), then exon 20 and beyond of the ALK gene would be upregulated (for example, have higher expression levels than the exons on the 3' side of the breakpoint). In another example, a different ALK gene exon could serve as a breakpoint and then all exons on the 5' side of the breakpoint would be upregulated. The systems and methods may be used to facilitate the detection of upregulation (increased expression level) or downregulation (reduced expression level) of some exons in ALK compared to other ALK exons in order to detect an ALK fusion and/or the location of the fusion breakpoint in the ALK gene. In one example, sequencing data from as few as one cDNA fragment may be used to detect a fusion variant and/or determine breakpoints for a fusion variant.

In various embodiments, the systems and methods optimize a probe set to provide more uniform coverage of each exon of the ALK gene to improve the signal to noise ratio such that the data may be used to generate more refined and accurate exon-level expression calls, or expression levels for the individual exons (for example, increasing the RNA expression level resolution to the scale of individual exons).

In various embodiments, in a somatic (for example, cancer or tumor) specimen, if the tumor purity is low (for example, only 10% or so), more uniform coverage/sensitivity is even more important for accurately analyzing sequencing data to detect variants.

In some embodiments, probes are targeted for sequencing antimicrobial resistance genes (AMR), antiviral drug resistance genes, or the genes targeted by antimicrobial therapeutics. Probes may consist of optimized probe sets for rare or novel drug resistance genes. Probes may consist of panels for specific coinfections, groups of related infectious agents, which may be grouped according to one or more of the following criteria: the infectious agents cause similar symptoms, affect similar geographical locations and/or anatomical areas, or have similar organism phylogeny. Application examples might include selection of cfDNA for detecting variation in drug resistant *Borrelia burgdorferi*, the causative agent for Lyme Disease (for an example of varying degrees of AMR in *Borrelia burgdorferi*, see Hodzic E, Bosnian Journal of Basic Medical Sciences, 7 Jul. 2015, 15(3):1-13 DOI: 10.17305/bjbms.2015.594 PMID: 26295288 PMCID: PMC4594320, the contents of which are incorporated herein by reference in their entirety). Typically Lyme disease can be an initial mild infection in the body and can be dormant and reactivated, causing unusual symptoms. The systems and methods could be applied to sequencing "persister" cases where infectious agents have a dormant metabolism, for example, as in the case of Lyme disease. In this example, the systems and methods may be used to 1) to increase the selection of genomic DNA or RNA transcripts from the target organism (for example, an infectious agent), 2) to selectively remove nucleic acids having a high copy number, high number of RNA transcripts or redundant DNA fragments from the sequencing library preparation 3) Select transcripts involved in host response to a pathogenic infection (IGF1, TLR9 gene in reference to Meningitis, host immune genes, etc.). For an example of the interaction between host immune response genes and pathogenicity of an infectious agent, see Sanders M S et al., Genes Immun. 2011 July; 12(5):321-34 (2011), the contents of which are incorporated herein by reference in their entirety for all purposes. In various embodiments, the combined effect of the sequencing library preparation strategies included in the systems and methods may allow for an increase in the ratio of desired targets of rare populations of RNA transcripts or DNA molecules in the subsequent sequencing reactions above the background level to increase detection of and the ability to call rare variants or coinfections. For an example of using NGS hybrid-capture in infectious diseases, see Gaudin and Desnues, Front Microbiol., 9:2924 (2018), the contents of which are incorporated herein in their entirety for all purposes. These could be used in the calling of viral or bacterial origin of infection (for example, detecting the presence of an infectious agent in a patient specimen and/or determining which infectious agent is the cause of a disease if multiple infectious agents are present). For an example of using host RNA expression levels to determine which infectious agent is responsible for disease, see Herberg J A et al., JAMA, 316(8):35-845 (2016), the contents of which are incorporated herein in their entirety for all purposes. The tuning of the AMR probe set to enrich rare sequence information may allow health system wide information (for example, data generated by multiple medical treatment centers and stored in a database) about AMR tracking as well. For an example of AMR tracking, including determining the genetic sequences in infectious agents associated with AMR, see Guitor et al., Antimicrob Agents Chemother, 64(1):e01324-19 (2019), the contents of which are incorporated herein in their entirety for all purposes. Additionally, capture probes can be developed for accessing host response to infection where limiting the conversion of highly expressed genes would allow for the selective capture of rare target or splice variants of RNA transcripts to be accessed to determine the host response to the causative agent, the location of the infection, or early indications of organ rejection due to infection.

In some embodiments, probes may be designed for panels of coinfections, panels of widely divergent organisms across many genera of distantly and/or closely related organisms. These may be used in immunocompromised individuals who could have an opportunistic infection with an organism that is rarely pathogenic. The panel could be comprised of probes for infectious agents for a genus that is unknown to be a pathogen, normal flora, or an emerging infectious disease. These organisms may be unculturable, and therefore would remain undetected with standard of care procedures. In one embodiment, an ideal application of co-infection panels would be for immunocompromised patients who may have several active infections, for example HIV positive patients with pneumonia could quickly be prescribed a course of therapy based on determination if the pneumonia is caused by methicillin resistant *Staphylococcus aureus*, multidrug-resistant *Streptococcus pneumoniae*, ciprofloxacin resistant *Pseudomonas aeruginosa*, or another microbe. In another example, patients who have received an organ transplant and are on drugs suppressing their immune system may benefit from a wide panel of probes targeting genes whose expression levels can be indicative of organ failure, each of which may be adjusted according to the systems and methods disclosed herein.

In various embodiments, the systems and methods optimize probe sets to achieve more uniform coverage of the fms-related tyrosine kinase 3 (FLT3) gene to facilitate detection of tandem repeats/duplications by NGS. Certain FLT3 tandem repeats may be associated with a prognosis, diagnosis, or matched therapy (for example, in an acute myeloid leukemia cancer specimen). For example, see Spencer D H et al., J Mol Diagn., 15(1):81-93 (2013), the contents of which are incorporated herein by reference in their entirety for any and all purposes. The systems and methods may report detected FLT3 tandem repeats and any associated prognosis, diagnosis, and/or matched therapies predicted to be effective in slowing the progression of AML or another disease.

In various embodiments, the systems and methods optimize probe sets to achieve more uniform coverage of t-cell receptor (TCR/BCR) or b-cell receptor (TCR/BCR) genes to give more accurate clonal population statistics, which may be used to characterize an immune repertoire; to monitor immune response, autoimmune disease, cancer progression, minimal residual disease (MRD), immunotherapy treatment; to design novel immunotherapies; or to predict susceptibility to various infectious diseases.

In various embodiments, the systems and methods may be used to make probes multi-use, achieving similar sensitivity of targets across various applications (e.g. solid tumor versus liquid biopsy, or targeted panel versus whole exome or whole genome), which may include adjusting a probe's ratio of capture moiety-conjugated probes for each panel.

In various embodiments, the systems and methods may include a 3 tool process that is run in series, wherein the three tools are: 1. Modify the activity of each probe without affecting the stoichiometry. Modifying the percent of probe biotinylation without changing the total molarity may allow for very accurate fine tuning of the activity. 2. Adjusting the relative probe concentrations to alter the relative recovered target through stoichiometry. 3. Adding more probes to the region (or probe design change).

In various embodiments, the systems and methods may be used in conjunction with sequencing DNA from solid, blood, liquid biopsy, or other specimens, or RNA. In various embodiments, the systems and methods may facilitate the more accurate detection of single nucleotide variants (SNVs), small INDELs, large INDELs, CNVs, pseudogenes, GC/AT rich regions of the genome, genetic rearrangements, splice variants, gene expression levels, aneuploidy, trisomy, and other possible conclusions based on genetic sequencing results. In various embodiments, the systems and methods may facilitate genetic analysis of genetic regions of interest of varying sizes, including point locations, small regions or elements, individual exon or intron, multiple exons or multiple introns, entire gene, partial chromosome, whole chromosome, etc. In various embodiments, the systems and methods may be utilized for genetic sequencing in the following categories: oncology/somatic, germline, infectious or parasitic disease, microbiome, other areas of human healthcare, etc.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in FIG. 1, and/or as described in FIG. 2. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for determining a genomic characteristic of a subject, the method comprising:
contacting a sample comprising nucleic acids from the subject with a composition comprising a first set of nucleic acid probes for determining a genomic characteristic of a first target region in a genome of a subject, wherein:
the first set of nucleic acid probes comprises a first plurality of nucleic acid probe species;
each respective nucleic acid probe species in the first plurality of nucleic acid probe species aligns to a different subsequence of the first target region of a reference genome for the species of the subject;
the composition comprises, for each respective nucleic acid probe species in the first plurality of nucleic acid probe species, a first amount of a first version of the respective nucleic acid probe species that is conjugated to a capture moiety and a second amount of a second version of the respective nucleic acid probe species that is not conjugated to a capture moiety;
the composition exhibits a first ratio, for a first respective nucleic acid probe species in the first plurality of the nucleic acid probe species that aligns to a first subsequence of the first target region, between (i) the first amount of the first version of the first respective nucleic acid probe species and (ii) the second amount of the second version of the first respective nucleic acid probe species;
the composition exhibits a second ratio, for a second respective nucleic acid probe species in the first plurality of the nucleic acid probe species that aligns to a second subsequence of the first target region, between (i) the first amount of the first version of the second respective nucleic acid probe species and (ii) the second amount of the second version of the second respective nucleic acid probe species; and the first ratio is different from the second ratio;
recovering a portion of the nucleic acids using an agent that binds to the capture moiety; and
sequencing the recovered portion of the nucleic acids, thereby identifying the genomic characteristic of the subject.

2. The method of claim 1, wherein the genomic characteristic is selected from the group consisting of a single nucleotide variant (SNV), an indel, a copy number variation (CNV), a pseudogene, a CG-rich region, an AT-rich region, a genetic rearrangement, a splice variant, a gene expression level, aneuploidy, and trisomy.

3. The method of claim 1, wherein the nucleic acids from the subject are obtained from a liquid biological sample from the subject.

4. The method of claim 3, wherein the liquid biological sample is a blood sample or a blood plasma sample from the subject.

5. The method of claim 1, wherein the nucleic acids from the subject are obtained from a solid biological sample from the subject.

6. The method of claim 5, wherein the solid biological sample is a tumor sample or a normal tissue sample from the subject.

7. The method of claim 1, wherein the nucleic acids comprise mRNA or cDNA generated from mRNA, the method further comprising, prior to contacting the sample with the composition, selectively removing a portion of the mRNA or cDNA from a first gene that is represented in the sample at a level that is greater than the representation of at least 50% of the genes represented in the sample.

8. The method of claim 7, wherein the first gene is represented in the sample at a level that is greater than the representation of at least 75% of the genes represented in the sample.

9. The method of claim 1, wherein the concentration of the first respective nucleic acid probe species in the first plurality of nucleic acid probe species is equal to the concentration of the second respective nucleic acid probe species in the first plurality of nucleic acid probe species.

10. The method of claim 1, wherein the concentration of each respective nucleic acid probe species in the first set of nucleic acid probes is equal in the composition.

11. The method of claim 1, wherein the concentration of the first respective nucleic acid probe species in the first plurality of nucleic acid probe sequences is not equal to the concentration of the second respective nucleic acid probe species in the first plurality of nucleic acid probe sequences.

12. The method of claim 1, wherein:
when the composition is used in a first reference nucleic acid pull-down and sequencing assay, difference between (i) the number of raw sequencing reads output for the first subsequence of the first target region and (ii) the number of raw sequencing reads output for the second subsequence of the first target region is less than the difference between (iii) the number of raw sequencing reads output for the first subsequence of the first target region in a second reference nucleic acid pull-down and sequencing assay and (iv) the number of raw sequencing reads output for the second subsequence of the first target region in the second reference nucleic acid pull-down and sequencing assay;
the first reference nucleic acid pull-down and sequencing assay and the second reference nucleic acid pull-down and sequencing assay are performed using the same methodology;
the second reference nucleic acid pull-down and sequencing assay is performed with a second composition comprising the first respective nucleic acid probe species and the second respective probe species; and
in the second composition, the percentage of the first respective nucleic acid probe species that are conjugated to the capture moiety and the percentage of the second respective nucleic acid probe species that are conjugated to the capture moiety are the same.

13. The method of claim 12, wherein the difference between (i) the number of raw sequencing reads output for the first subsequence of the first target region and (ii) the number of raw sequencing reads output for the second subsequence of the first target region is at least 75% less than the difference between (iii) the number of raw sequencing reads output for the first subsequence of the first target region in the second reference nucleic acid pull-down and sequencing assay and (iv) the number of raw sequencing reads output for the second subsequence of the first target region in the second reference nucleic acid pull-down and sequencing assay.

14. The method of claim 1, wherein:
when the composition is used in a reference nucleic acid pull-down and sequencing assay, the assay outputs for each respective nucleic acid probe species in the first plurality of nucleic acid probe species a corresponding number of raw sequence reads, thereby forming a first distribution of numbers of raw sequence reads for the respective subsequences of the first target region that align with a respective nucleic acid probe species in the first set of nucleic acid probes; and
the range of the first distribution is less than 100% percent of the median of the distribution.

15. The method of claim 1, wherein:
when the composition is used in a reference nucleic acid pull-down and sequencing assay, the assay outputs for each respective nucleic acid probe species in the first plurality of nucleic acid probe species a corresponding number of raw sequence reads, thereby forming a first distribution of numbers of raw sequence reads for the respective subsequences of the first target region that align with a respective nucleic acid probe species in the first set of nucleic acid probes; and
the first distribution has a fold-80 score of less than 1.5.

16. The method of claim 1, wherein:
when the composition is used in a reference nucleic acid pull-down and sequencing assay, the assay outputs for each respective nucleic acid probe species in the first plurality of nucleic acid probe species a corresponding number of raw sequence reads, thereby forming a first distribution of numbers of raw sequence reads for the respective subsequences of the first target region that align with a respective nucleic acid probe species in the first set of nucleic acid probes;
the range of the first distribution is less than the range of a second distribution;
the second distribution is determined by using a second composition in the reference nucleic acid pull-down and sequencing assay to output, for each respective nucleic acid probe species in the first plurality of nucleic acid probe species, a corresponding number of raw sequence reads, thereby forming the second distribution of numbers of raw sequence reads for the respective subsequences of the first target region that align with a respective nucleic acid probe species in the first set of nucleic acid probes;

in the second composition, the percentage of each respective nucleic acid probe species in the first plurality of nucleic acid probe species that are conjugated to the capture moiety is the same.

17. The method of claim 16, wherein the range of the first distribution is at least 50% less than the range of the second distribution.

18. The method of claim 16, wherein the fold-80 score of the first distribution is at least 50% less than the fold-80 score of the second distribution.

19. The method of claim 1, wherein the first plurality of nucleic acid probe species is at least 10 nucleic acid probe species.

20. The method of claim 1, wherein the first target region comprises a gene selected from the group consisting of BRCA1, BRCA2, a CYP gene, CYP2D, a PMS2 pseudogene, a PMSCL pseudogene, DMD, MET, TP53, ALK, IGF1, TLR9, FLT3, and a TCR/BCR gene.

21. The method of claim 1, wherein the capture moiety is biotin.

22. The method of claim 1, wherein the composition further comprises a second set of nucleic acid probes for identifying a genomic characteristic of a second target region in the genome of the subject:
the second set of nucleic acid probes comprises a second plurality of nucleic acid probe species;
each respective nucleic acid probe species in the second plurality of nucleic acid probe species aligns to a different subsequence of the second target region of the reference genome for the species of the subject;
the composition comprises, for each respective nucleic acid probe species in the second plurality of nucleic acid probe species, a first amount of a first version of the respective nucleic acid probe species that is conjugated to the capture moiety and a second amount of a second version of the respective nucleic acid probe species that is not conjugated to a capture moiety;
the composition exhibits a third ratio, for a first respective nucleic acid probe species in the second plurality of the nucleic acid probe species that aligns to a first subsequence of the second target region, between (i) the first amount of the first version of the first respective nucleic acid probe species and (ii) the second amount of the second version of the first respective nucleic acid probe species;
the composition exhibits a fourth ratio, for a second respective nucleic acid probe species in the second plurality of the nucleic acid probe species that aligns to a second subsequence of the second target region, between (i) the first amount of the first version of the second respective nucleic acid probe species and (ii) the second amount of the second version of the second respective nucleic acid probe species; and
the third ratio is different from the fourth ratio.

23. The method of claim 22, wherein the concentration of the first respective nucleic acid probe species in the second plurality of nucleic acid probe species is equal to the concentration of the second respective nucleic acid probe species in the second plurality of nucleic acid probe species.

24. The method of claim 22, wherein the concentration of the first respective nucleic acid probe species in the second plurality of nucleic acid probe species is equal to the concentration of the first respective nucleic acid probe species in the first plurality of nucleic acid probe species.

25. The method of claim 22, wherein the concentration of the first respective nucleic acid probe species in the second plurality of nucleic acid probe species is not equal to the concentration of the first respective nucleic acid probe species in the first plurality of nucleic acid probe species.

26. The method of claim 22, wherein the concentration of the first respective nucleic acid probe species in the second plurality of nucleic acid probe species is not equal to the concentration of the second respective nucleic acid probe species in the second plurality of nucleic acid probe species.

27. The method of claim 22, wherein the first ratio is different from the third ratio and the fourth ratio.

28. The method of claim 22, wherein the second ratio is different from the third ratio and the fourth ratio.

29. The method of claim 22, wherein the concentration of each respective nucleic acid probe species in the second set of nucleic acid probes is equal in the composition.

30. The method of claim 22, wherein:
when the composition is used in a reference nucleic acid pull-down and sequencing assay, the assay outputs for each respective nucleic acid probe species in the second plurality of nucleic acid probe species a corresponding number of raw sequence reads, thereby forming a second distribution of numbers of raw sequence reads for the respective subsequences of the second target region that align with a respective nucleic acid probe species in the second set of nucleic acid probes; and
the range of the second distribution is less than 100% of the median of the distribution.

31. The method of claim 22, wherein:
when the composition is used in a reference nucleic acid pull-down and sequencing assay, the assay outputs for each respective nucleic acid probe species in the second plurality of nucleic acid probe species a corresponding number of raw sequence reads, thereby forming a second distribution of numbers of raw sequence reads for the respective subsequences of the second target region that align with a respective nucleic acid probe species in the second set of nucleic acid probes; and
the second distribution has a fold-80 score of less than 1.5.

* * * * *